(12) United States Patent
Baird et al.

(10) Patent No.: US 8,021,298 B2
(45) Date of Patent: Sep. 20, 2011

(54) SYSTEM AND METHOD FOR MAPPING PAIN DEPTH

(75) Inventors: John C. Baird, South Pomfret, VT (US); John R. Arscott, Northants (GB)

(73) Assignee: Psychological Applications LLC, South Pomfret, VT (US)

( * ) Notice: Subject to any disclaimer, the term of this patent is extended or adjusted under 35 U.S.C. 154(b) by 1118 days.

(21) Appl. No.: 11/769,993

(22) Filed: Jun. 28, 2007

(65) Prior Publication Data

US 2009/0005649 A1 Jan. 1, 2009

(51) Int. Cl.
*A61B 5/00* (2006.01)
*A61B 19/00* (2006.01)
*G09G 5/00* (2006.01)
*G06K 9/00* (2006.01)

(52) U.S. Cl. ........ 600/300; 600/301; 600/557; 345/581; 345/619; 382/165; 382/181; 434/262; 434/267

(58) Field of Classification Search .................. None
See application file for complete search history.

(56) References Cited

U.S. PATENT DOCUMENTS

| | | | |
|---|---|---|---|
| 4,671,772 A | 6/1987 | Slade et al. | |
| 5,720,502 A | 2/1998 | Cain | |
| 5,778,882 A | 7/1998 | Raymond | |
| 5,882,203 A | 3/1999 | Correa et al. | |
| 5,908,383 A | 6/1999 | Brynjestad | |
| 5,984,368 A * | 11/1999 | Cain | 283/115 |
| 6,007,340 A | 12/1999 | Morrel-Samuels | |
| 6,132,218 A * | 10/2000 | Benja-Athon | 434/267 |
| 6,314,405 B1 | 11/2001 | Richardson | |
| 6,405,159 B2 | 6/2002 | Bushey et al. | |
| 6,529,195 B1 | 3/2003 | Eberlein | |
| 6,684,276 B2 | 1/2004 | Walker et al. | |
| 6,856,315 B2 | 2/2005 | Eberlein | |
| 6,929,607 B2 | 8/2005 | Lipman | |
| 7,362,334 B2 * | 4/2008 | Daignault, Jr. | 345/581 |
| 7,374,536 B1 * | 5/2008 | Taylor | 600/300 |
| 7,671,874 B2 * | 3/2010 | Daignault, Jr. | 345/619 |
| 2003/0139652 A1 * | 7/2003 | Kang et al. | 600/300 |
| 2005/0214727 A1 * | 9/2005 | Stoianovici et al. | 434/262 |

OTHER PUBLICATIONS

U.S. Office Action mailed Nov. 8, 2005 received in corresponding U.S. Appl. No. 10/662,568, 9 pgs.
U.S. Office Action mailed May 26, 2006 received in corresponding U.S. Appl. No. 10/662,568, 10 pgs.
The Engineer Online, "3D model helps patients track pain", Nov. 9, 2006, 2 pgs.

(Continued)

*Primary Examiner* — Eric F Winakur
*Assistant Examiner* — Shirley Jian
(74) *Attorney, Agent, or Firm* — Grossman Tucker Perreault & Pfleger, PLLC

(57) ABSTRACT

A pain depth mapping system and method may be used to map the location and depth of pain experienced by a user (e.g., a patient). The pain depth mapping system and method is capable of displaying one or more body representations with symptom representations representing the location of the pain. The pain depth mapping system and method allows the user to delineate one or more user-defined pain depth regions on a cross-section of the body representation with the symptom representations to form a pain map. The symptom mapping system and method may also allow the user to vary the pain intensity represented by the symptom representations as the user delineates the user-defined pain depth region(s).

21 Claims, 14 Drawing Sheets

OTHER PUBLICATIONS

Beyer, J. E. (1984). "The Oucher": a User's Manual and Technical Report. Evanston, IL: Judson Press, 1-13.

Bieri, D., and others (1990). The Faces Pain Scale for the self-assessment of the severity of pain experienced by children: development, initial validation, and preliminary investigation for the ratio scale properties, Pain, 41 (2), 139-150.

Buchanan, L., Voigtman, J., & Mills, H. (1997). Implementing the agency for health care policy and research pain management pediatric guideline in a multicultural practice setting. J. Nurs. Care Qual., 11(3), 23-35.

Keck, J. F., Gerkensmeyer, J. E., Joyce, B. A., & Schade, J. G. (1996). Reliability and validity of the faces and word descriptor scales to measure procedural pain. Journal of Pediatric Nursing, 11(6), 368-374.

McGrath, P. A., & Gillespie, J. (2001). Pain assessment in children and adolescents (pp. 97-118). In (D. C. Turk & R. Melzack, Eds.) Handbook of pain assessment, 2nd edition, The Guilford Press: New York.

McRae, M. E., Rourke, D. A., Imperial-Perez, F. A., Eisenrigh, C. M., & Ueda, J. N. (1997). Development of a research-based standard for assessment, intervention, and evaluation of pain after neonatal and pediatric cardiac surgery. Pediatric Nursing, 23(3), 263-271.

Sporrer, K. A., Jackson, S. M., Agner, S., Laver, J., & Abboud, M. R. (1994). Pain in children and adolescents with sickle cell anemia: a prospective study utilizing self-reporting. The American Journal of Pediatric Hematology/Oncology, 16(3), 219-224.

Tyler, D., Douthit, A., & Chapman, C. (1993). Toward validation of pain measurement tools for children: a pilot study. Pain, 52, 301-309.

West, N., Oakes, L, and others (1994). Measuring pain in pediatric oncology ICU patients. Journal of Pediatric Oncology Nursing, 11(2), 64-68.

Wong, D. L. (1999). Whaley & Wong's nursing care of infants and children (6th edition). St. Louis, MO: Mosby Year-Book, 1045-1057.

Wong, D. L, & Baker, C. (1988). Pain in children: comparison of assessment scales, Pediatr. Nurs. 14(1), 9017, 9-17.

Baird, J. C. & Noma, E. (1978), Fundamentals of Scaling and Psychophysics, Chap. 1, John Wiley & Sons: New York, 1-10.

Stevens, S. S. (1946) On the theory of scales of measurement. Science, 103, 677-680.

Beyer, Judith E., (1992) The Creation, Validation, and Continuing Development of the Oucher: A Measure of Pain Intensity in Children, Journal of Pediatric Nursing, vol. 7, No. 5, 335-346.

U.S. Office Action dated Mar. 17, 2010 issued in related U.S. Appl. No. 11/553,051.

* cited by examiner

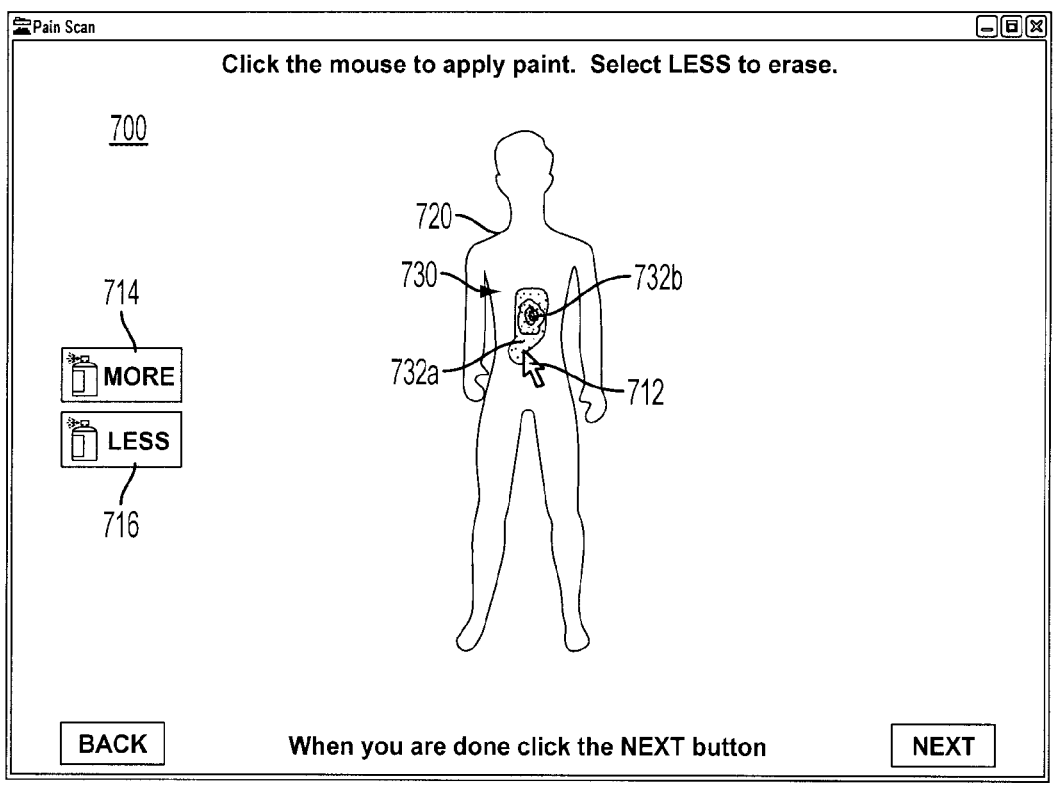
FIG. 7
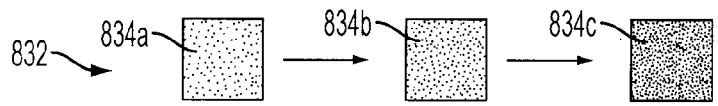
FIG. 8
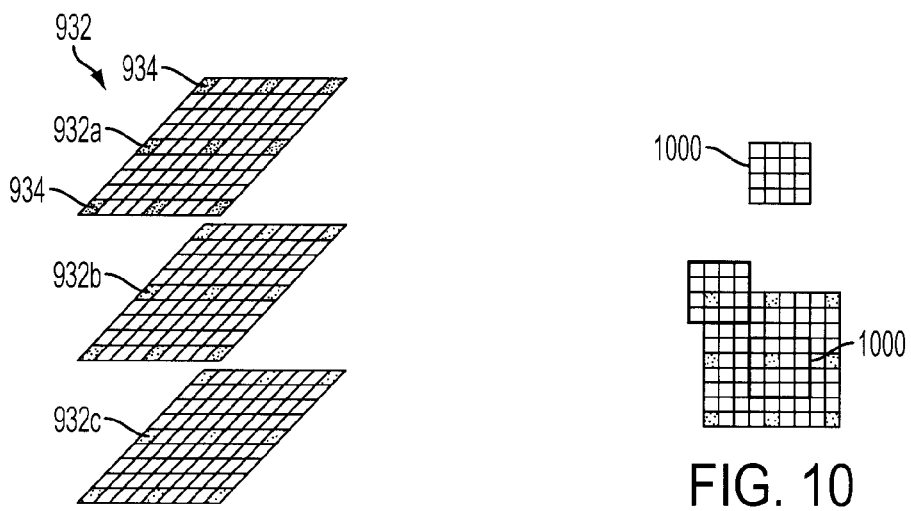
FIG. 9
FIG. 10

SYSTEM AND METHOD FOR MAPPING PAIN DEPTH

STATEMENT REGARDING FEDERALLY SPONSORED RESEARCH OR DEVELOPMENT

This invention was made with government support under SBIR grant Nos. 2 R44 MH62833-02A2, and 1 R43 HD052324-01A1 awarded by the National Institutes of Health. The Government has certain rights in the invention.

CROSS-REFERENCE TO RELATED APPLICATIONS

This application is related to U.S. patent application Ser. No. 11/553,051, filed Oct. 26, 2006, which is a continuation-in-part of U.S. patent application Ser. No. 10/662,568, filed on Sep. 15, 2003, which is a divisional of U.S. patent application Ser. No. 10/016,623, filed on Dec. 10, 2001, now U.S. Pat. No. 6,619,961, which claims the benefit of U.S. Provisional Application Ser. No. 60/270,854, filed Feb. 23, 2001, and U.S. Provisional Patent Application Ser. No. 60/292,115, filed on May 18, 2001, all of which are fully incorporated herein by reference.

TECHNICAL FIELD

The present invention relates to representing and recording perceived symptoms on different parts of the body, and more particularly, to a system and method for mapping pain depth at user-defined locations on a body representation.

BACKGROUND INFORMATION

For many years, patients with medical symptoms, such as pain, itchiness, and soreness, have been asked by health practitioners to designate the locations of their symptoms on pictures of the human body represented as silhouettes, for example, on a piece of cardboard or paper. In one common application, the McGill pain questionnaire, patients express the location of their symptoms by marking with a pen or pencil on front and back views of the human body. In a variation on this method, the Brief Pain Inventory also asks patients to place an X on the body diagram to represent the most painful location.

A major drawback of paper-and-pencil approaches to representing the location and intensity of pain on body diagrams is that there is no intuitive way to simultaneously indicate symptom location along with a grade of symptom intensity. Patients may not have the skill required to color areas of the body to represent intensities accurately, for example, using color or patterns. Also, there is no standard set of visual symbols to represent different levels or grades of intensity. With symptoms like pain, these existing techniques also do not allow the patient to map the depth of the pain within the body. These methods also limit the ability to fine-tune or change ratings. These methods are further limited in that the data generated by the patient is not automatically entered into a computer in a manner that allows results to be manipulated, analyzed, or displayed on a monitor for viewing by the attending physician or other health care professional.

More recently, computer programs have been developed to allow the patient to mark locations of pain on a diagram of the human body displayed on a monitor. One existing computerized method uses predefined visual icons to represent different types and intensities of pain, which requires the user to first select an icon from a palette and then drag the icon to a location on the diagram. Another computerized method allows a user to select predefined areas on a diagram of the human body. Such existing methods limit the user's ability to define a region of pain, the intensity of the pain, and the depth of the pain in a simple and precise manner.

BRIEF DESCRIPTION OF THE DRAWINGS

These and other features and advantages will be better understood by reading the following detailed description, taken together with the drawings wherein:

FIG. 7 is a screen shot generated by a symptom mapping system using symptom representations to represent both location and intensity of symptoms on a body representation, consistent with another embodiment of the present invention.

FIG. 8 is a schematic diagram of another embodiment of a symptom representation including a dot having a varying shade to represent symptom intensity.

FIG. 9 is a schematic diagram of a further embodiment of a symptom representation including a pattern of dots having varying shade to represent symptom intensity.

FIG. 10 is a schematic diagram of a template used to determine color density within a symptom region, consistent with a further embodiment of the present invention.

DETAILED DESCRIPTION

A symptom mapping system and method, consistent with embodiments of the present invention, may be used to map the location, intensity and/or depth of pain experienced by a user (e.g., a patient). As will be described in greater detail below, the symptom mapping system and method is capable of displaying one or more body representations with user-defined symptom regions formed by symptom representations representing both the location and intensity of the symptoms. The symptom mapping system and method allows the user to select the locations of the symptom representations to delineate one or more user-defined symptom regions on the body representation, forming a symptom map. The symptom mapping system and method may also allow the user to vary the intensity represented by the symptom representations as the user delineates the user-defined symptom region. The symptom mapping system and method may further allow the user to map the depth of pain at any selected location on the body representation.

Figure 1:
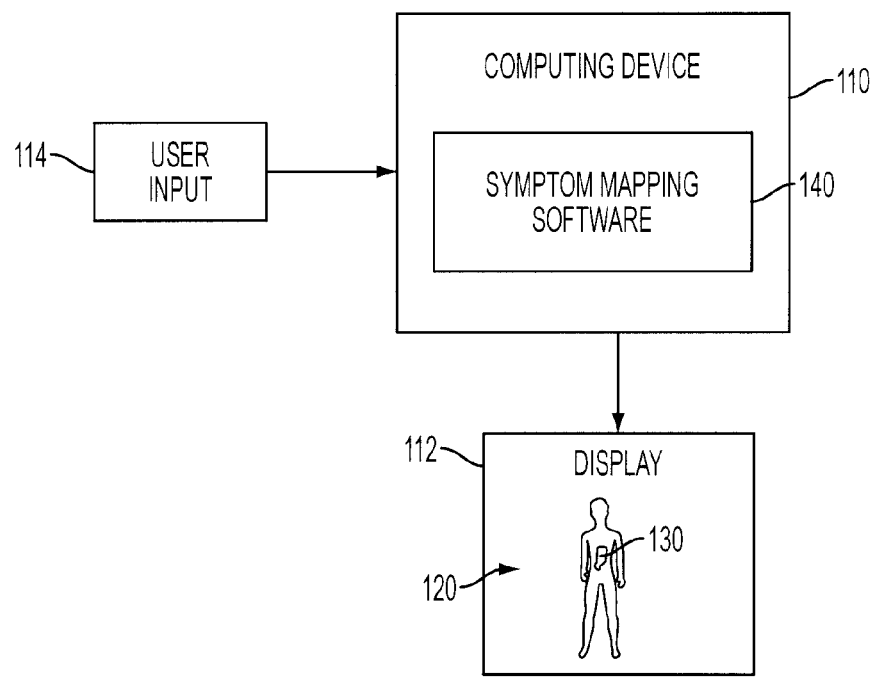
FIGS. 1 and 2 are schematic block diagrams of computerized systems for mapping location and intensity of symptoms, consistent with embodiments of the present invention.
Figure 2:
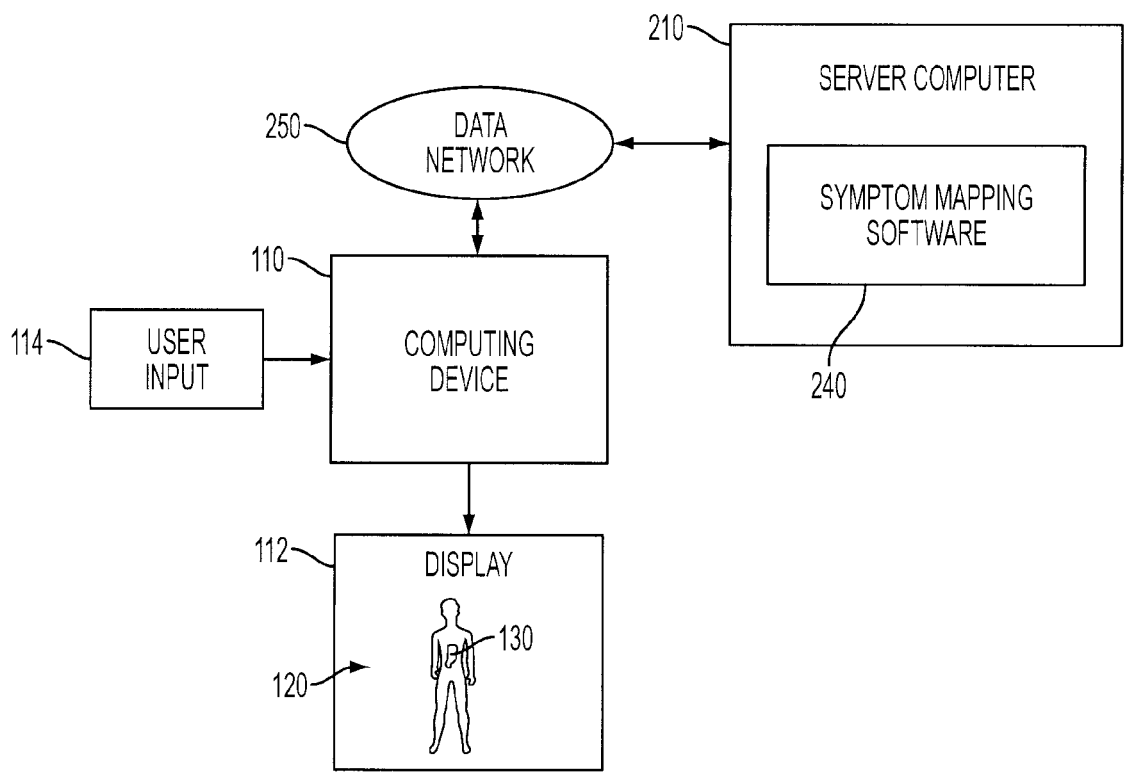

Referring to FIGS. 1 and 2, one embodiment of a symptom mapping system and method may be implemented using a computing device 110, such as a personal computer (e.g., a desktop or a laptop computer) or a handheld computer (e.g., a personal digital assistant) including a display 112 and one or more input devices 114 coupled to the computing device 110. The display 112 may be used to display information to the user, such as one or more body representation(s) 120 and user-defined symptom region(s) 130. The user input device 114 may be used to provide a user input to the computing device 110, for example, to manipulate the body representation 120 and to delineate the user-defined symptom region(s) 130 on the body representation 120 to form the symptom map. The user input device 114 may include a mouse, a keyboard, joystick, a stylus, or a separate remote control device. To generate the user input, the user input device 114 may be capable of moving an indicator (e.g., a cursor or other icon) across user-selected locations (e.g., corresponding to symptom locations on the body representation 120 on the display 112) while the user input device 114 is activated. In one example, a mouse may be used to move a cursor or other icon across the display 112 while depressing the mouse button. In another example, a stylus or finger may be moved across the display 112 while in contact with the display 112.

Embodiments of the symptom mapping system and method may be implemented as software or a computer program product for use with the computing device 110. Such implementation may include, without limitation, a series of computer instructions that embody all or part of the functionality described herein with respect to the symptom mapping system and method. The series of computer instructions may be stored in any machine-readable medium, such as semiconductor, magnetic, optical or other memory devices, and may be transmitted using any communications technology, such as optical, infrared, microwave, or other transmission technologies. Such a computer program product may be distributed as a removable machine-readable medium (e.g., a diskette, CD-ROM), preloaded with a computer system (e.g., on system ROM or fixed disk), or distributed from a server or electronic bulletin board over the network (e.g., the Internet or World Wide Web). Alternative embodiments of the invention may be implemented as pre-programmed hardware elements or as a combination of hardware, software and/or firmware.

In one embodiment, shown in FIG. 1, the instruction sets and subroutines of the symptom mapping software 140 may be stored on a storage device in or coupled to the computing device 110 and may be executed by one or more processors (not shown) and one or more memory architectures (not shown) incorporated into the computer device 110. The storage device may be, for example, a hard disk drive, a tape drive, an optical drive, a RAID array, a random access memory (RAM), or a read-only memory (ROM). In one embodiment, the symptom mapping system may be implemented as one or more executable files generated using programming techniques and languages (e.g., Basic) known to a programmer of ordinary skill in the art. Those skilled in the art will recognize that various file formats, authoring programs, and/or programming languages may be used to create a software implementation of the symptom mapping system. The computing device 110 may also store the resulting symptom map and any data related to the symptom map (e.g., patient information). The computing device 110 may also store any files including text, images, videos, or audio clips used to interact with the user.

In another embodiment, shown in FIG. 2, symptom mapping software 240 may also reside on a separate computer 210 coupled to a data network 250, such as a local area network, a wide area network, an intranet, or the Internet. The separate computer 210 may be a web server running a network operating system, such as Microsoft Windows XP Server™, Novell Netware™, or Redhat Linux™ and may also execute a web server application, such as Microsoft IIS™, Novell Webserver™, or Apache Webserver™, that allows for HTTP (i.e., HyperText Transfer Protocol) access to the separate computer 210 via the network 250. In this embodiment, a user may use a desktop application (e.g., Microsoft Internet Explorer™, Netscape Navigator™, or a specialized interface) on the computing device 110 to access the symptom mapping software 240 residing on the separate computer 210 via the network 250. In this embodiment, at least a portion of the symptom mapping software 240 may be executed on the computing device 110, for example, as an Active X® control, a Java™ Applet, or a Macromedia Flash® file, as the user uses the symptom mapping system. The server computer 210 may also store the resulting symptom map and any data related to the symptom map (e.g., patient information). The server computer 210 may also store any files including text, images, videos, or audio clips used to interact with the user.

Figure 3:
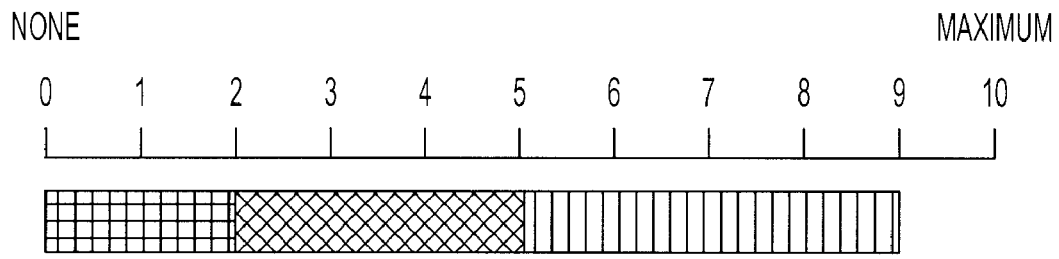
FIG. 3 is a schematic diagram of body representations including symptom regions using color to represent symptom intensity, consistent with one embodiment of the present invention.
Figure 3:
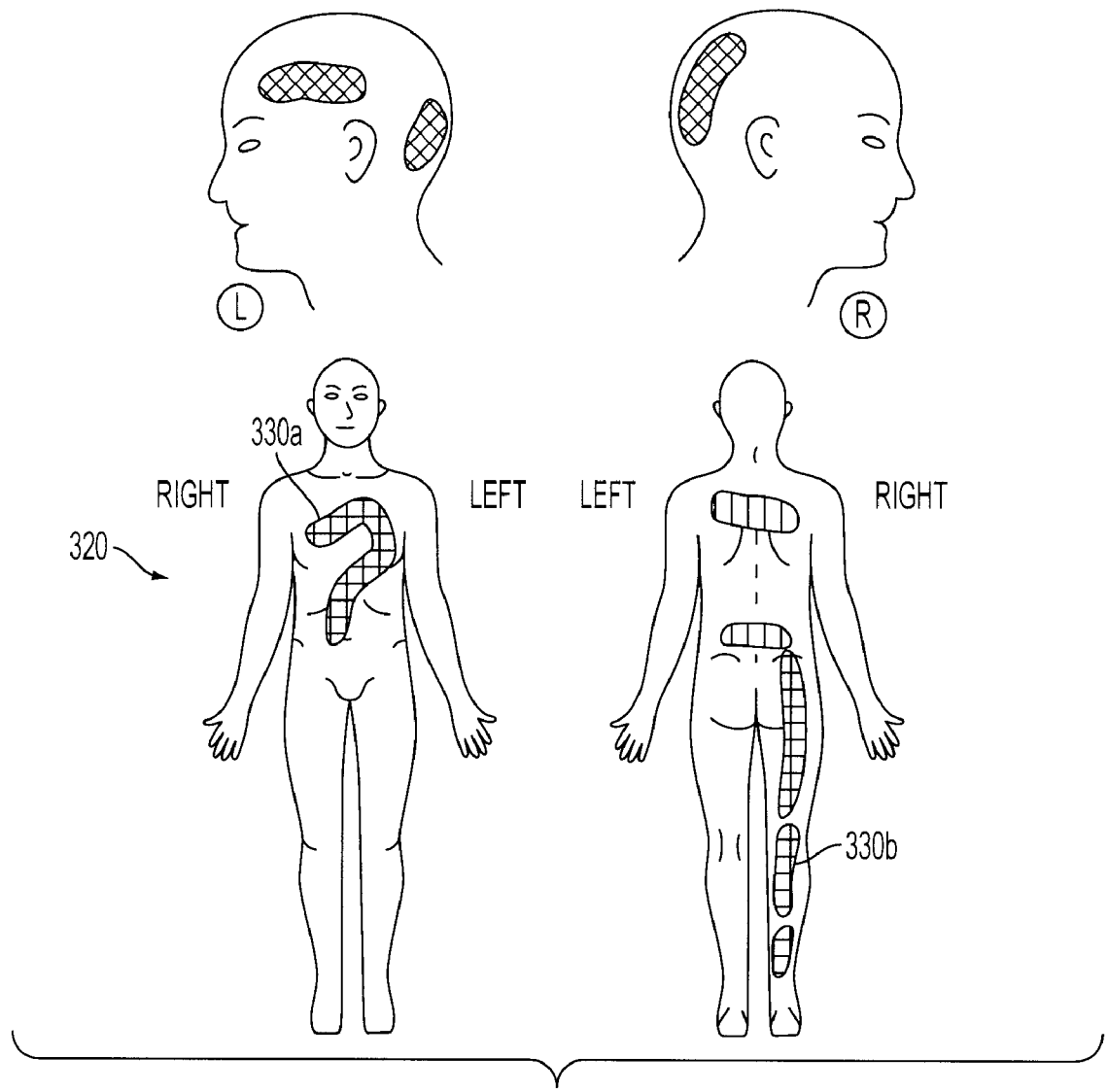

Referring to FIG. 3, one embodiment of a system and method of mapping symptoms is described in greater detail. According to this exemplary method, the user is a patient experiencing a sensory symptom such as pain or itchiness. The sensory symptoms may be represented and recorded within a physical context such as one or more body representations 320 corresponding to a patient's body. In the illustrated embodiment, the system may display the body representation(s) 320 as outline drawings of a human head and body. With a user input device, the user may delineate one or more user-defined symptom regions 330a, 330b indicating the locations of sensory symptoms such as pain or itchiness.

According to this embodiment, activating a user input device (e.g., depressing the mouse) results in the appearance of a symptom representation, such as a solid figure (square, circle, or some other geometric figure) at the location of a cursor controlled by the user input device. The size of the figure used for the symptom representation can be adjusted to accommodate the size of the entire drawing as it appears on the computer screen. If the user input device is continuously activated (e.g., by holding down the mouse button) while moving an indicator (e.g., a cursor) across user-selected locations on the body representation, symptom representations (e.g., solid figures) may be displayed at the user-selected locations as the indicator is moved. The user may thus delineate user-defined symptom regions 330a, 330b at least partially filled in with the symptom representations to indicate the exact pattern of locations on the body representation 320 where the symptom is experienced. One or more user-defined symptom regions may be delineated to form a symptom map.

According to one embodiment, the system may only display symptom representations that do not overlap with adjacent symptom representations so that the system does not have multiple records of the same (or almost the same) placement location. A library of "legal" points or locations (i.e., those falling within the confines of the figure) can be stored separately, and checked by the software before displaying a symptom representation at a location or point indicated by the user. The user can also erase any inadvertent designations. Different colors or types of geometric figures can be used to represent different types of sensory symptoms (e.g., different types or intensities of pain) in a physical context. As shown in the exemplary embodiment in FIG. 3, patients can record their symptoms at different intensities on the body picture using different colors to represent the different intensities (as indicated by the scale), thereby providing a symptom scanning technique.

The symptom mapping system may also record the order of the placement of each symptom representation on the body representation 320, for example, by recording the x,y coordinates of each symptom representation placed at a user-selected location on the body representation 320. The system may also record the times between each designation of a location or point on the drawing. This data allows an investigator to exactly reproduce the judgment process employed by the user in marking locations on the body representation 320. The recorded judgment data and judgment process data may thus be used to evaluate the patient's condition. In one example, an animated graphical representation showing the judgment process can be replayed (e.g., as a movie) to visualize the exact manner in which the user made each judgment. In another example, the data can be compared to previously recorded data for other patients, which has been stored in a library of data, to give a likely diagnosis for consideration by the physician.

Figure 4:
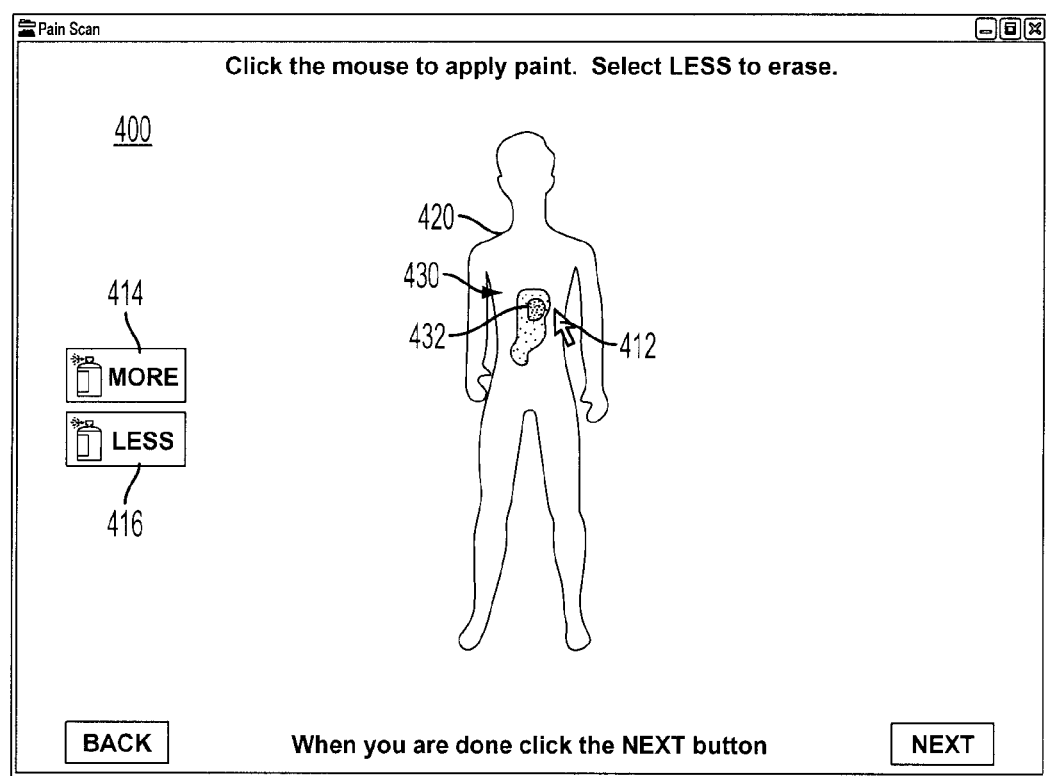
FIG. 4 is a screen shot generated by a symptom mapping system using symptom representations to represent both location and intensity of symptoms on a body representation, consistent with another embodiment of the present invention.

Referring to FIG. 4, another embodiment of a symptom mapping system and method is described in greater detail. According to this embodiment, a symptom mapping system may generate and display a symptom mapping screen 400 (e.g., using a computing device and display) including one or more body representations 420 representing one or more portions of a human body. Although the body representation 420 includes an outline of the entire body form, a body representation may also include only a portion (e.g., a head or hand) of the body. A body representation may also be enlarged to include additional details, such as a hand representation including all of the fingers on a hand. Enlarged body representations showing one or more body portions may be displayed separately or together with the body representation 420 showing the entire body form. Multiple body representations showing different views of a body or portions of a body may also be displayed together or separately. A body representation may also be displayed as a three-dimensional image, as described in greater detail below.

This embodiment of the symptom mapping system may allow the user to define one or more symptom regions 430 formed by symptom representations 432 displayed on the body representation 420. A user input device may be used to control the movement of an indicator (e.g., a cursor 402) on the screen 400 such that the symptom representations 432 may be displayed as the indicator moves across user-selected locations. The user may thus delineate the user-defined symptom region(s) 430, which may be at least partially filled with the symptom representations 432. In one embodiment, the indicator may be a cursor 402 or other icon displayed on the symptom mapping screen 400 and moved by an input device such as a mouse. In another embodiment, the indicator may correspond to a tip of an input device, such as a stylus or a finger, which may be moved across the screen 400 while in contact with the screen 400.

In one embodiment, the symptom mapping system may only display symptom representations 432 within the boundaries of the body representation 420. The symptom mapping system may identify locations on the screen 400 that are outside of the boundaries defined by the outline of the body representation(s) 420. If a user moves the indicator (e.g., the cursor 402) to any of these outside locations while activating the user input device, the symptom mapping system will not allow symptom representations to be displayed at those outside locations. The symptom mapping system may thus prevent the inaccuracy of the user from resulting in invalid symptom representations that do not designate a location on the body.

The colors of the body representation 420 and the symptom representations 432 may be contrasting such that the user can easily distinguish the user-defined symptom region(s) 430 displayed on the body representation(s) 420. For example, the body representation(s) 420 may be displayed with a gray or flesh color and the symptom representations 432 may be displayed with a red color. Those of ordinary skill in the art will recognize that other colors may be used. The symptom mapping system may also allow a user to define the colors of the body representation 420 and/or the symptom representations 432 based upon the user preferences. Different colors may also be used to indicate different characteristics of the symptoms, for example, to indicate different types of symptoms, different intensities of symptoms, and/or different dates associated with the mapping of the symptoms.

This embodiment of the symptom mapping system may also allow the user to define the intensity of the symptoms as the symptom regions 430 are defined. The intensity of the symptoms may be represented by the color density of the symptom region(s) 430, and the symptom mapping system may allow the user to control the color density at the user-selected locations. The color density of the symptom region(s) 430 may be related to the number of times that the indicator (e.g., the cursor 402) passes over a user-selected location while a user input device is activated and/or the amount of time that the indicator is activated while being held over a user-selected location.

Figure 5:
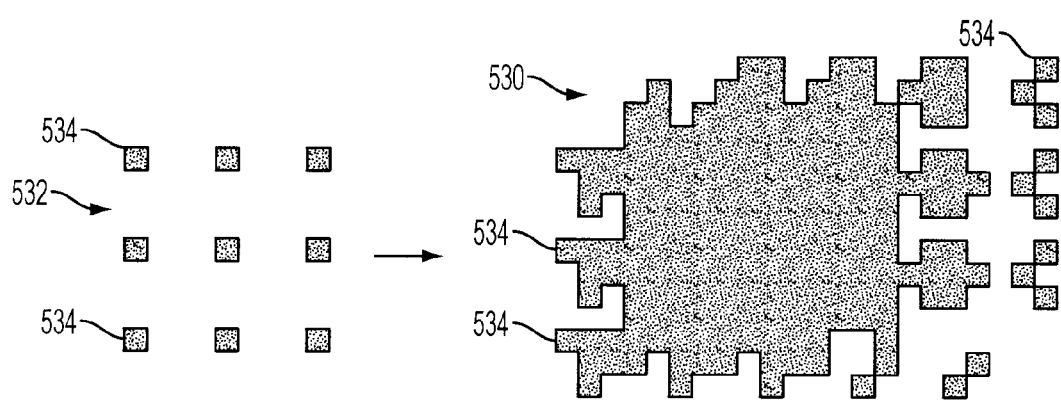
FIG. 5 is a schematic diagram of one embodiment of a symptom representation and a symptom region formed by a plurality of the symptom representations with the number of dots representing symptom intensity.

According to one embodiment, shown in FIG. 5, a user-defined symptom region 530 may be formed by symptom representations 532 that include a pattern of one or more spaced dots 534 and the color density may be based on the number of dots 534 displayed within an area. Each of the dots 534 may include a pixel or group of pixels of a predefined color. Each pattern of dots 534 may be displayed at a user-selected location in response to the user input, for example, in a manner similar to the airbrush feature of Microsoft® Paint. Although the illustrated embodiment of the symptom representation 532 includes a pattern of nine dots 534, other patterns and numbers of dots may also be used.

To define intensity, the user may control the number of symptom representations 532 displayed at user-selected locations as the indicator is moved on a body representation while activating the user input device. A single "click" of a mouse, for example, may result in a single symptom representation 532 (e.g., one pattern of dots) displayed at the location of the indicator. A continuous depression of the mouse button may result in multiple symptom representations 532 "filling in" at least a portion of the user-defined symptom region 530. When the number of symptom representations 532 displayed within the user-defined symptom region 530 increases, the dots 534 of the symptom representations 532 merge and the color density increases. Thus, the color density may be varied throughout a user-defined symptom region 530 by moving the indicator more frequently over some user-selected locations than other user-selected locations such that more dots 534 displayed together indicate higher color density (and higher symptom intensity) and less dots 534 displayed together indicate lower color density (and lower symptom intensity). The use of symptom representations 532 including a pattern of dots 534 allows the density to be gradually increased in a graded manner as the indicator moves over user-selected locations on a body representation.

Referring back to FIG. 4, one embodiment of the symptom mapping system may also allow the user to control the color density by selectively increasing or decreasing the color density of the symptom region(s) 430. The symptom mapping screen 400 may include intensity controls, such as more and less buttons 414, 416, to control whether or not the color density is increased or decreased when the user input device is activated. When the more button 414 is selected, a color density within the symptom region 430 may be increased at user-selected locations as the indicator passes over the user-selected locations when a user input device is activated. When the less button 416 is selected, a color density of the symptom region 430 may be decreased at user-selected locations as the indicator passes over the user-selected locations when a user input device is activated.

In the embodiment described above, the color density of the symptom region 430 may be decreased by deleting or erasing symptom representations 432 at the user selected locations. As shown in FIG. 5, for example, if a symptom representation 532 including a pattern of dots 534 is used, the same pattern of dots may be erased when the indicator moves over user-selected locations at which symptom representations 532 are displayed. Thus, the symptom representations 532 forming the user-defined symptom region 530 may be selectively erased by reducing in a graded manner the number of dots 534 that are displayed.

Figure 6A:
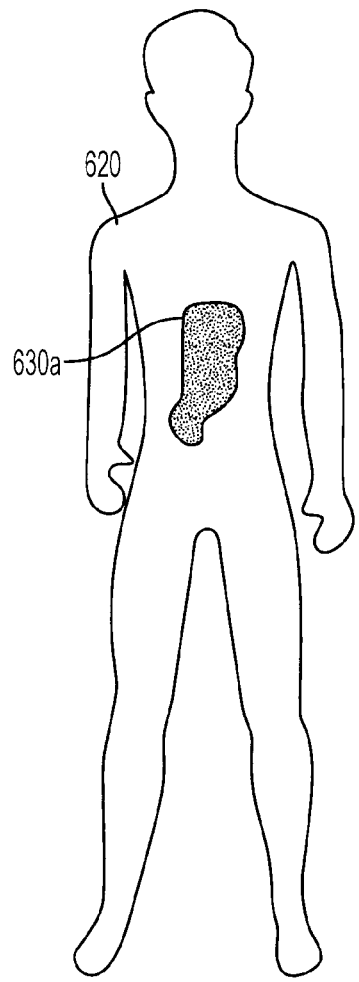
FIGS. 6A-6C are front views of a body representation including a symptom region with decreasing numbers of dots illustrating decreasing symptom intensity, consistent with one embodiment of the present invention.
Figure 6B:
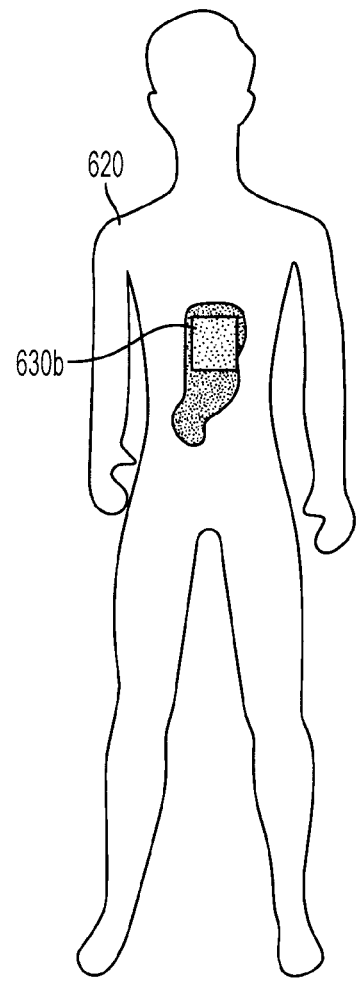
Figure 6C:
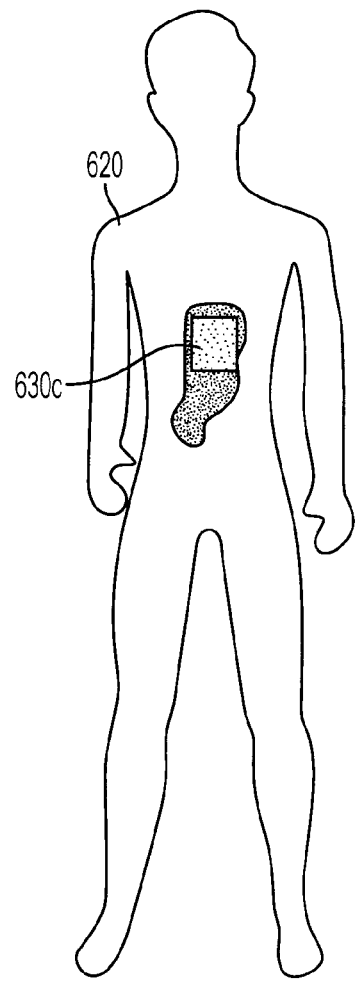

FIGS. 6A-6C show a body representation 620 including user-defined symptom regions 630a-630c with decreasing color density. In this example, a user may initially define the symptom region 630a shown in FIG. 6A to represent a symptom, such as pain, in the abdominal region. If the user decides that the symptom has a lesser intensity within a part of the symptom region 630a, the user may selectively decrease the density by erasing some of the symptom representations to define the symptom region 630b shown in FIG. 6B or by erasing more of the symptom representations to define the symptom region 630c shown in FIG. 6C. As shown, erasing symptom representations in this manner results in a gradual reduction of the color density rather than completely erasing a portion of the symptom region.

Referring to FIG. 7, one embodiment of the symptom mapping system may allow a user to define symptom intensity using color density based on the shade of symptom representations 732a, 732b forming a symptom region 730 on a body representation 720. As shown, symptom representations 732a of a lighter shade may indicate a lower grade intensity of the symptom and symptom representations 732b of a darker shade may indicate a higher grade intensity of the symptom. The user may selectively increase or decrease the shade of the symptom representations 732a, 732b within the symptom region 730 as the indicator (e.g., cursor 712) is moved over the user-selected locations while activating a user input device. In this embodiment, intensity controls, such as more and less buttons 714, 716, on the symptom mapping screen 700 may be used to control whether or not the shade increases or decreases when the user input device is activated. After selecting the more button 714, for example, movement of the indicator (e.g., the cursor 712) while activating the user input device may cause symptom representations to be displayed and/or the shade to be increased at user-selected locations. After selecting the less button 716, movement of the indicator (e.g., the cursor 712) while activating the user input device may cause the shade to be decreased and/or symptom representations to be deleted at user-selected locations.

As shown in FIG. 8, a symptom representation 832 using shade to define symptom intensity may include at least one dot 834a-834c having a predefined color and variable shade. The shade may vary from a dot 834a with a lightest shade to a dot 834b with a darker shade to a dot 834c with a darkest shade. In one example, each symptom representation 832 may include 6 shades. The shades may change as the user input device is activated when an indicator is held over a location of the symptom representation 832. A lighter shade dot 834a may change to a darker shade dot 834b or 834c, for example, by depressing a mouse button while holding a cursor continuously over a location or by repeatedly passing a cursor over the location while depressing the mouse button.

As shown in FIG. 9, a symptom representation 932 using shade to define symptom intensity may also include a pattern of spaced-apart dots 934 that have a predefined color and variable shade. The shade may vary from a symptom representation 932a with a lightest shade to a symptom representation 932b with a darker shade to a symptom representation 932c with a darkest shade. According to this embodiment, the symptom intensity may be represented by both the number of dots within an area and the shade of the dots. Using color density (e.g., number of dots and/or shade of dots) to represent symptom intensity allows a user to define symptom locations and intensity simultaneously. Those skilled in the art will recognize that the spacing, size, color and shade of the dots used for a symptom representation may vary depending upon a particular application.

One embodiment of the symptom mapping system may also determine the color density within portions of user-defined symptom regions to measure the relative symptom intensity represented therein. As shown in FIG. 10, color density may be determined using a template 1000 including a predefined array of dots or pixels, which may be passed over locations on a body representation. A density value may be calculated for each location of the template 1000. The density value may be based on the number of dots or pixels within the template 1000 and/or the shade values (e.g., gray scale values) of the dots or pixels within the template. If the template 1000 covers a 4×4 array of pixels and the symptom representations have six (6) possible shades, for example, the density value may be an integer between 0 and 96 for any location of the template 1000 on the body representation. If the template 1000 covers a 4×4 array of pixels and different shades are not used, the density value may be an integer between 0 and 16. In one example, the template 1000 may be passed over the body representation in steps of one or more pixels and the density value at each location of the template 1000 may be calculated and stored, for example, with coordinate data representing the location. In another embodiment, the relative symptom intensity may be measured only by determining the shade values for each dot or pixel displayed.

Figure 11A:
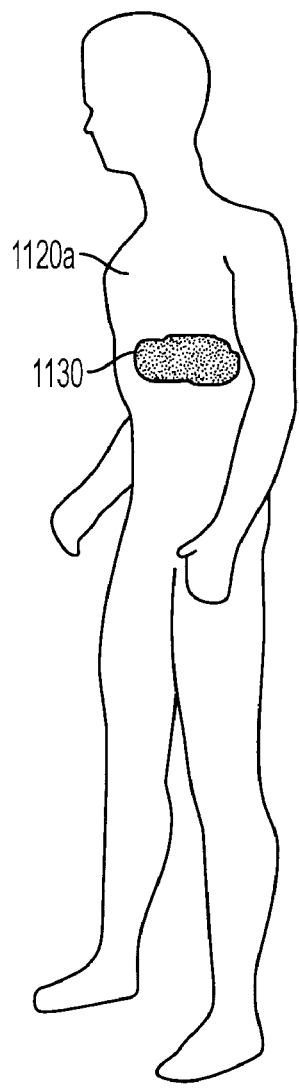
FIGS. 11A-11C are different views of a three-dimensional body representation including a symptom map, consistent with yet another embodiment of the present invention.
Figure 11B:
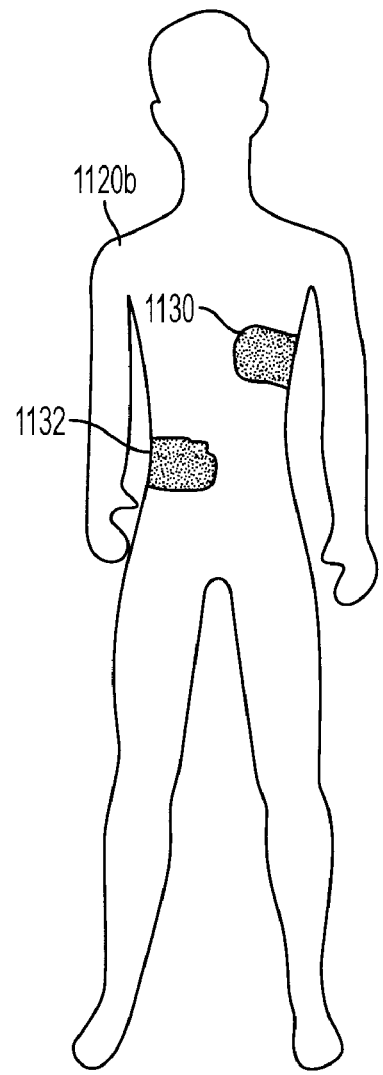
Figure 11C:
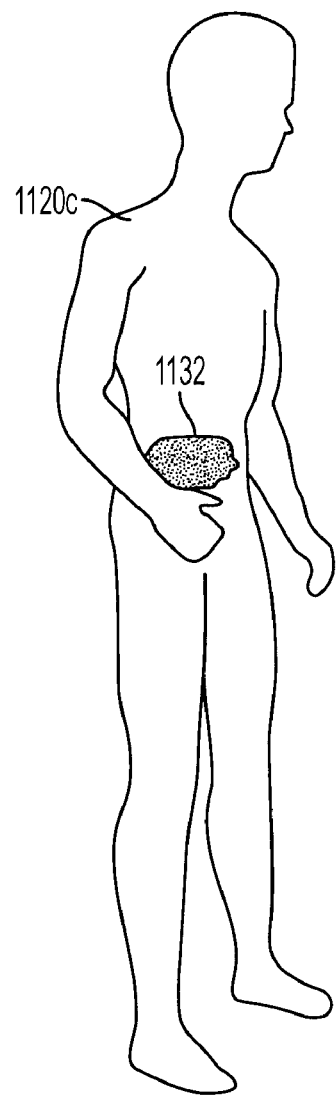

Referring to FIGS. 11A-11C, the symptom mapping system and method may also display one or more three-dimensional body representations 1120a-1120c with different positions or views showing different perspectives of the three-dimensional body representation(s) 1120a-1120c. FIG. 11A shows a three-dimensional body representation 1120a from a left side perspective. FIG. 11B shows a three-dimensional body representation 1120b from a front side perspective. FIG. 11C shows a three-dimensional body representation 1120c from a right side perspective. Those skilled in the art will recognize that other perspectives of a three-dimensional body representation may also be shown and other portions of a body (e.g., a hand or a head) may be shown as a three-dimensional representation.

User-defined symptom regions 1130, 1132 may be delineated on any one of the different perspectives of the three-dimensional body representations 1120a-1120c in the same way as described above (e.g., by causing symptom representations to be displayed at user-selected locations). The symptom mapping system may prevent the symptom representations forming the symptom regions 1130, 1132 from being displayed outside the boundaries of the body representation for any particular view or perspective of the three-dimensional body representations 1120a-1120c. The relative intensities within the symptom regions 1130, 1132 may also be measured by calculating color densities within any of the symptom regions 1130, 1132 for any view or perspective of the three-dimensional body representations 1120a-1120c.

Symptom regions 1130, 1132 that have been delineated on one particular view or perspective of a three-dimensional body representation may be carried over and shown in each of the different views or perspectives. The symptom region 1130, for example, may be delineated on the three-dimensional body representation 1120a from the left side perspective shown in FIG. 11A and may be shown on the three-dimensional body representation 1120b from the front side perspective shown in FIG. 11B. The symptom regions 1130, 1132 may also be modified (e.g., by erasing or decreasing the shade of symptom representations) in any one of the different views or perspectives in the same way as described above. A user may thus map symptom location and intensity from a variety of viewpoints to develop a more accurate and complete symptom map.

Figure 12:
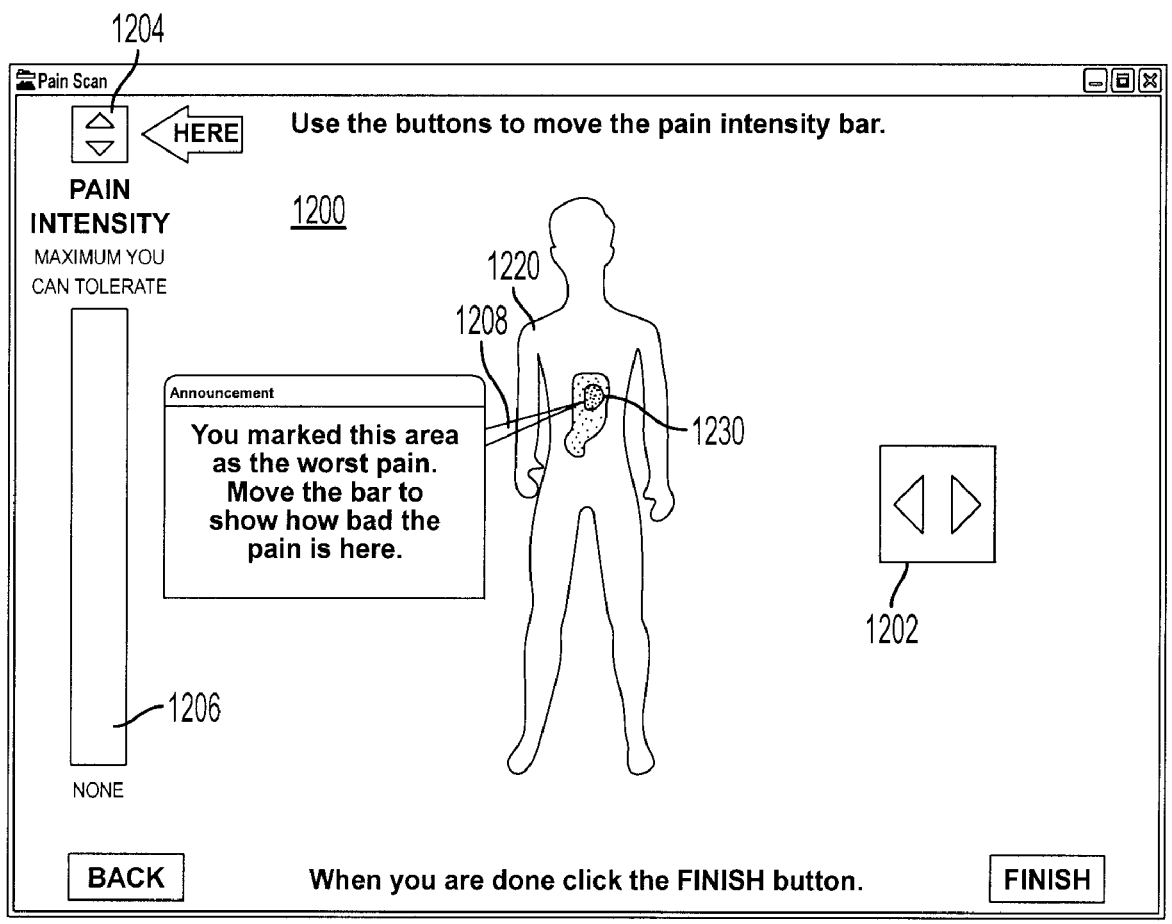
FIG. 12 is a screen shot generated by a symptom mapping system using a rating scale to calibrate symptom intensity, consistent with a further embodiment of the present invention.

As shown in FIG. 12, one embodiment of the symptom mapping system may generate a symptom mapping screen 1200 that includes a movement control 1202 (e.g., movement control arrows) that controls the movement of a three-dimensional body representation 1220 in one or more directions. A user may thus select the desired view or perspective of the three-dimensional body representation 1220 to reveal areas where the user experiences the symptom. A user input device may be used to activate the movement control 1202 to generate a user input indicating a direction and amount of movement of the three-dimensional body representation 1220. In response to the user input, the symptom mapping system may display an ordered series of static views from different angles of observation corresponding to the direction of movement, thereby simulating animated movement of the body representation 1220. The symptom mapping system may stop at a user-selected view of the body representation 1220 based on the amount of movement indicated by the user input. In one embodiment, for example, using the cursor to activate an arrow on the movement control 1202 causes the three-dimensional body representation 1220 to rotate about a vertical axis such that the three-dimensional body representation 1220 may be selectively rotated 360° in each direction. Those skilled in the art will recognize that a three-dimensional body representation may be rotated or moved in other directions and in other ways.

Figure 13A:
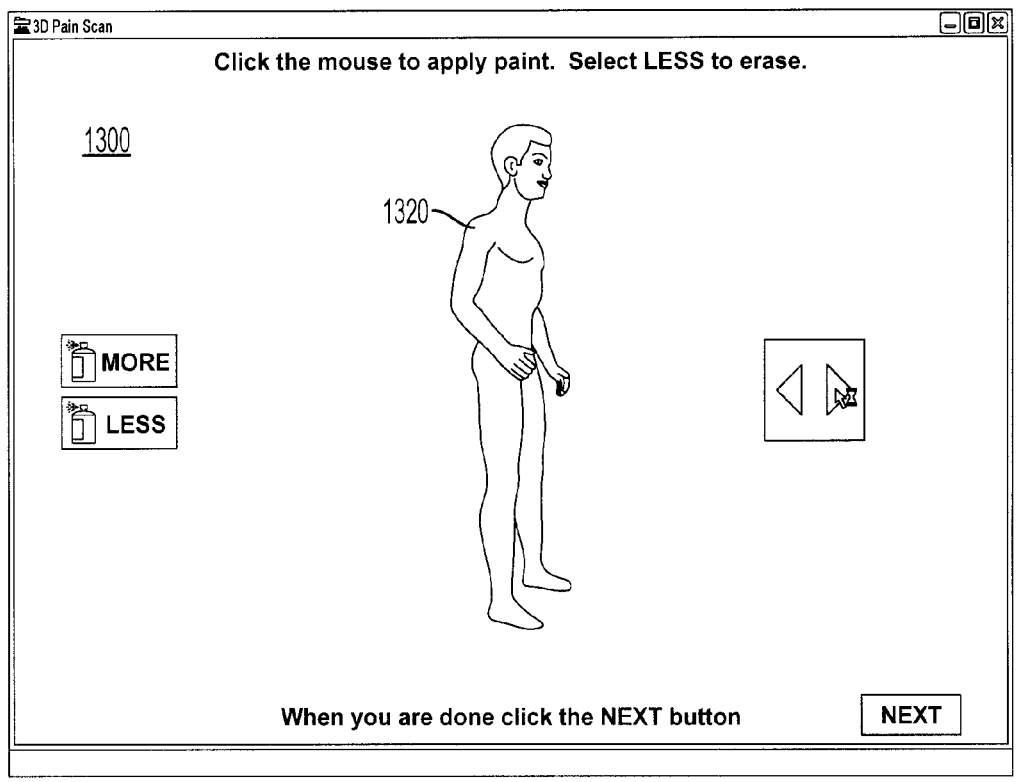
FIGS. 13A and 13B are screen shots generated by a symptom mapping system using a three-dimensional body representation, consistent with yet another embodiment of the present invention.
Figure 13B:
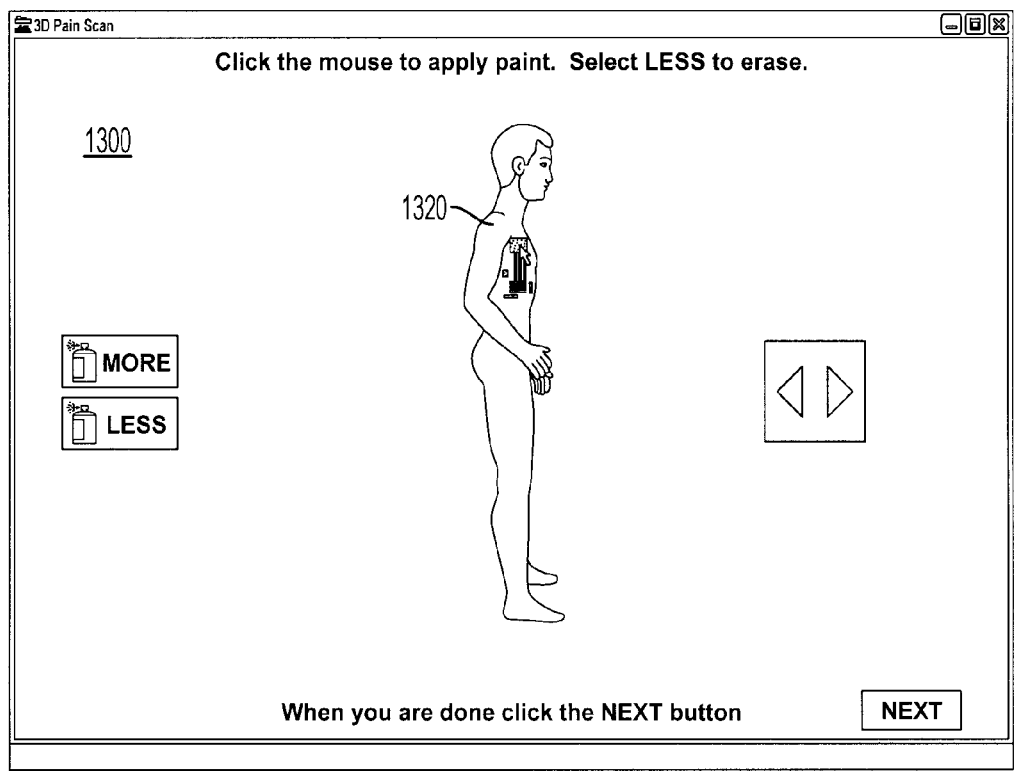

FIGS. 13A and 13B illustrate a symptom mapping screen 1300 generated by a further embodiment of the symptom mapping system. According to this embodiment, a three-dimensional body representation 1320 may include a representation of the body surfaces in addition to an outline of the body, thereby providing a more realistic representation of a human body. In one embodiment, the three-dimensional body representation 1320 may be made up of thirty-six (36) different images or views separated by about ten (10) degrees to provide the perception of actual rotation of the body or parts thereof. The different image views that make up the three-dimensional body representation 1320 may be generated and stored as image files used by a computing device to generate the movable three-dimensional representation 1320. The different views used may be obtained using known software products for generating three-dimensional graphics, such as the product available under the name Poser from Curious Labs or the product available under the name 3-D Studio Max.

One embodiment of the symptom mapping system and method may also be capable of calibrating the symptom intensity represented by the user-defined symptom regions on a body representation. To calibrate the symptom intensity, the symptom mapping system may request that the user input a symptom intensity rating associated with a location of highest relative intensity on the body representation. In one embodiment, a highest intensity location is identified for the user by the symptom mapping system, for example, using the method described above for measuring the relative intensity by calculating color density values. The user may also manually select a highest intensity location to be used in performing the calibration.

As shown in FIG. 12, for example, the symptom mapping system may identify the location of the highest relative intensity (e.g., the worst pain) on a user-defined symptom region 1230 after the user has completed the process of defining symptom regions on the body representation 1220. The screen 1200 may include, for example, a visual indicator 1208 pointing to the highest intensity location on the body representation 1220. If a three-dimensional body representation 1220 is used, the body representation 1220 may be rotated or moved until the highest intensity location is displayed to the user.

In this embodiment, the symptom mapping screen 1200 generated by the symptom mapping system may include a visual analog scale 1206 (e.g., a sliding bar) used to indicate a symptom intensity rating. The visual analog scale 1206 may include labels or descriptors at each end (e.g., from "NONE" to "MAXIMUM YOU CAN TOLERATE") and/or along the entire scale (e.g., mild, moderate, severe) to indicate the intensity ratings to the user. An indicator (e.g. a cursor) may be used directly on the scale 1206 to slide the bar to the selected rating or may be used to activate a scale adjustment control 1204 (e.g., up and down arrows) that causes the bar to move along the scale 1206. Numerical intensity values (e.g., in a range between 0 for NONE and 10 for MAXIMUM) may be associated with the locations on the visual analog scale 1206. Although not shown in the exemplary embodiment, numerical intensity values may be shown along the scale 1206 instead of or in addition to verbal descriptors. In other embodiments, a user may directly enter a numerical value to input a symptom intensity rating or may select a verbal descriptor associated with a numerical intensity value.

After the user has selected a final symptom intensity rating on the visual analog scale 1206, the numerical intensity value (or scaled intensity value) associated with the selected intensity rating may be associated with the highest relative intensity indicated on the symptom region 1230. This numerical intensity value associated with the selected symptom intensity rating may then be used to calibrate the relative intensity of the other locations on the symptom region 1230 by assigning scaled intensity values associated with the scale 1206 to the other locations, for example, based on the density values measured for the other locations compared to the density value for the highest relative intensity location. Locations on the body representation 1220 that do not include any symptom region may be assigned a scaled intensity value of zero.

Figure 14:
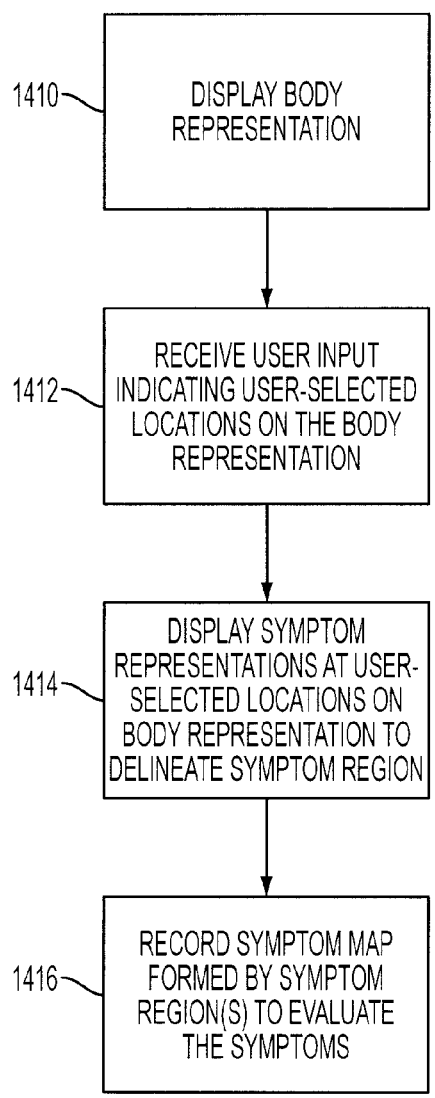
FIG. 14 is a flow chart illustrating one embodiment of a symptom mapping method.

FIG. 14 illustrates one embodiment of a symptom mapping method that may be used to map the location of symptoms experienced by a user. This embodiment of the symptom mapping method includes displaying 1410 one or more body representations. The body representation may be displayed as a two-dimensional or a three-dimensional body representation representing at least a portion of a user's body, as described above. The method may also include receiving 1412 a user input indicating user-selected locations on the body representation. The user-selected locations may correspond to the location of an indicator, such as a cursor, controlled by a user input device while the user input device is activated. The method may further include displaying 1414 symptom representations at the user-selected locations on the body representation to delineate at least one symptom region. The symptom representations may include solid figures having a color indicating intensity of the symptom or may include a pattern of dots with color density indicating intensity of the symptom, as described above. The method may further include recording 1416 a symptom map formed by the symptom regions to evaluate the symptoms. Recording a symptom map may include recording image files and/or data (e.g., coordinates of symptom representations) used to recreate the symptom map including the body representation and the symptom region(s) defined on the body representation. Other data associated with the symptom map (e.g., patient data) may also be recorded.

Figure 15:
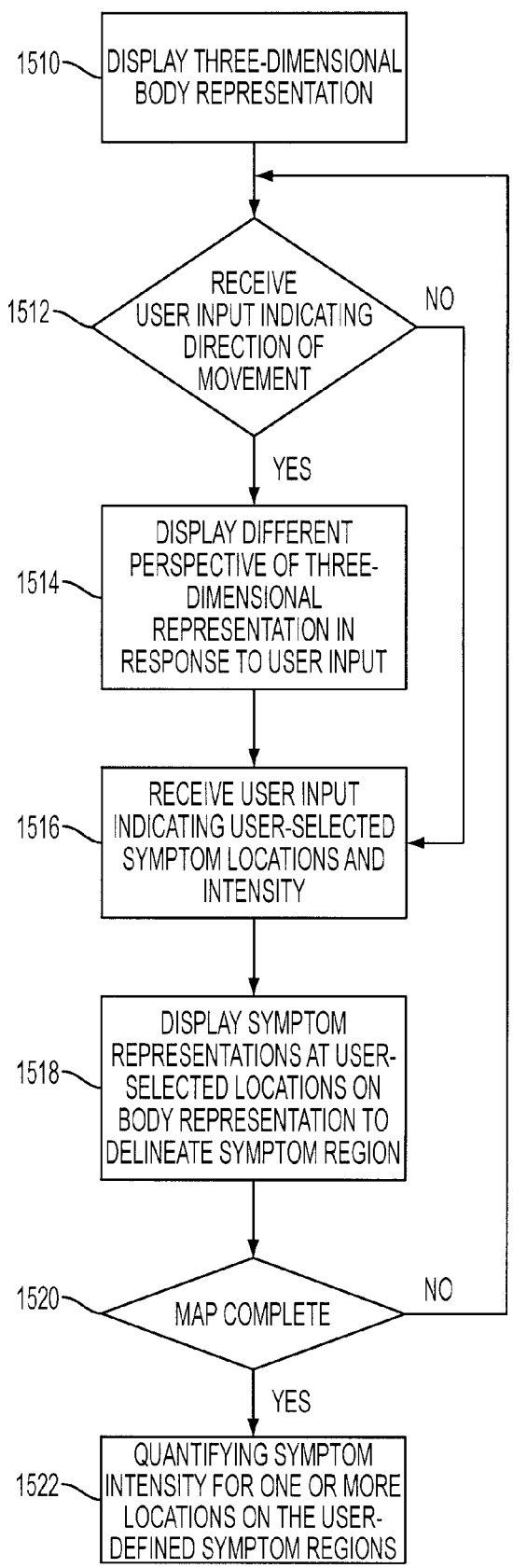
FIG. 15 is a flow chart illustrating another embodiment of a symptom mapping method.

FIG. 15 illustrates another embodiment of a symptom mapping method that may be used to map the location and intensity of symptoms experienced by a user. This embodiment of the symptom mapping method includes displaying 1510 a three-dimensional body representation representing at least a portion of the user's body. In response to receiving 1512 user input indicating direction of movement, the method may display 1514 a different perspective of the three-dimensional body representation. Different perspectives of the three-dimensional body representation may be displayed until the user selects a desired perspective. The three-dimensional body representation may be rotated, for example, until the desired perspective is displayed, as described above.

This embodiment of the symptom mapping method may further include receiving 1516 a user input indicating both user-selected symptom locations and intensity. The user-selected locations may correspond to the location of an indicator (e.g., a cursor) controlled by a user input device while the user input device is activated (e.g., by depressing a mouse button). The symptom intensity may correspond to the duration of activation of a user input device when the indicator appears over user-selected locations and/or the number of times the indicator passes over user-selected locations. In response to receiving the user input, the method displays 1518 symptom representations at the user-selected locations to delineate user-defined symptom representations. The symptom representations may include one or more dots with symptom intensity being represented by the number of the dots within an area and/or by the shade of the dots.

The user may continue this process until the symptom map is complete 1520 (i.e., the user has finished defining symptom regions). When a symptom map is complete 1520, the method may include quantifying 1522 the symptom intensity for one or more locations on the user-defined symptom region(s). In one embodiment, the symptom intensity may be quantified by measuring relative intensity values (e.g., by calculating density values) for one or more locations within the user-defined symptom regions on the symptom map. The symptom intensity may also be quantified by calibrating relative symptom intensity values within the symptom regions based on a symptom intensity rating input by the user, as described above.

After completing the symptom map and quantifying the symptom intensity, the symptom mapping system and method may record the symptom map and any associated data. In one embodiment, a user may indicate that the symptom map is completed (e.g., using a finish button on the screen), causing the final symptom map and associated data to be recorded. The symptom mapping system and method may record both the graphical image or images representing the symptom map and/or the numerical data that may be used to recreate the symptom map. The numerical data may include the coordinates (e.g., x, y coordinates), shade values, and associated intensity values (e.g., a relative intensity value and/or a calibrated intensity value) associated with each symptom representation, each dot, or other selected locations within a user-defined symptom region. The symptom mapping system and method may also record other information (e.g., a user's name, the date, etc.) to be associated with the completed symptom map.

Embodiments of the symptom mapping system and method may store recorded data in a database, for example, to generate a library of symptom maps associated with different users. After a diagnosis is made relative to a particular symptom map, diagnosis information may also be stored with the symptom map in the database. A symptom mapping system and method may thus compare new symptom maps with a database or library of symptom maps to obtain a possible diagnosis. A symptom map including symptom regions in certain locations on a body representation may be indicative of a particular type of illness or disorder. In one example, a symptom map within a database may indicate a particular pattern of pain symptoms including a high intensity of chest pain and pain in the left arm and an actual diagnosis of a heart attack for the patient associated with the symptom map. If a new symptom map indicates a similar pattern of high intensity chest and left arm pain, the system may indicate the possible diagnosis of a heart attack after comparing the new symptom map with the symptom maps in the database and determining that the symptom map is similar to the stored symptom map indicating a diagnosis of heart attack.

Embodiments of the symptom mapping system and method may also include recording the user's actions over time to allow the process of generating the symptom map to be displayed. The symptom mapping system may record, for example, each movement of a three-dimensional body representation and each change in symptom location and intensity (e.g., the coordinates and intensity values of each symptom representation) displayed on a body representation. The recorded symptom mapping process, or portions of the symptom mapping process, may then be displayed as an animated sequence (e.g., as a movie) to show how the user arrived at a particular symptom map. In one embodiment, the changes in symptom location and intensity over time may be displayed for a particular perspective view of a three-dimensional body representation. In another embodiment, the changes in symptom location and intensity over time may be displayed for all views of the three-dimensional body representation, for example, for one complete rotation of the body representation. By displaying the process of generating a symptom map (e.g., as an animated sequence), the judgment process of the user (e.g., the patient) in assessing pain may be visualized and evaluated.

Embodiments of the symptom mapping system and method may also allow a user to generate a symptom map at one time (e.g., at one visit to a pain clinic) and to modify and/or add to the symptom map at other times (e.g., at subsequent visits to the pain clinic). The changes made to the symptom map during each of these different times may be recorded by the symptom mapping system. The recorded symptom mapping process may then be displayed, for example, by displaying an animated sequence showing the symptom regions generated and/or modified during each successive time or visit. In one example, one rotation of the three-dimensional body representation may show the changes in symptom location and intensity over time for one visit and subsequent rotations may show the changes over time for subsequent visits. Animating the progress of location and intensity information over time may provide an attending physician with a useful diagnostic tool for assessing symptom (e.g., pain) reports from patients.

Figure 16:
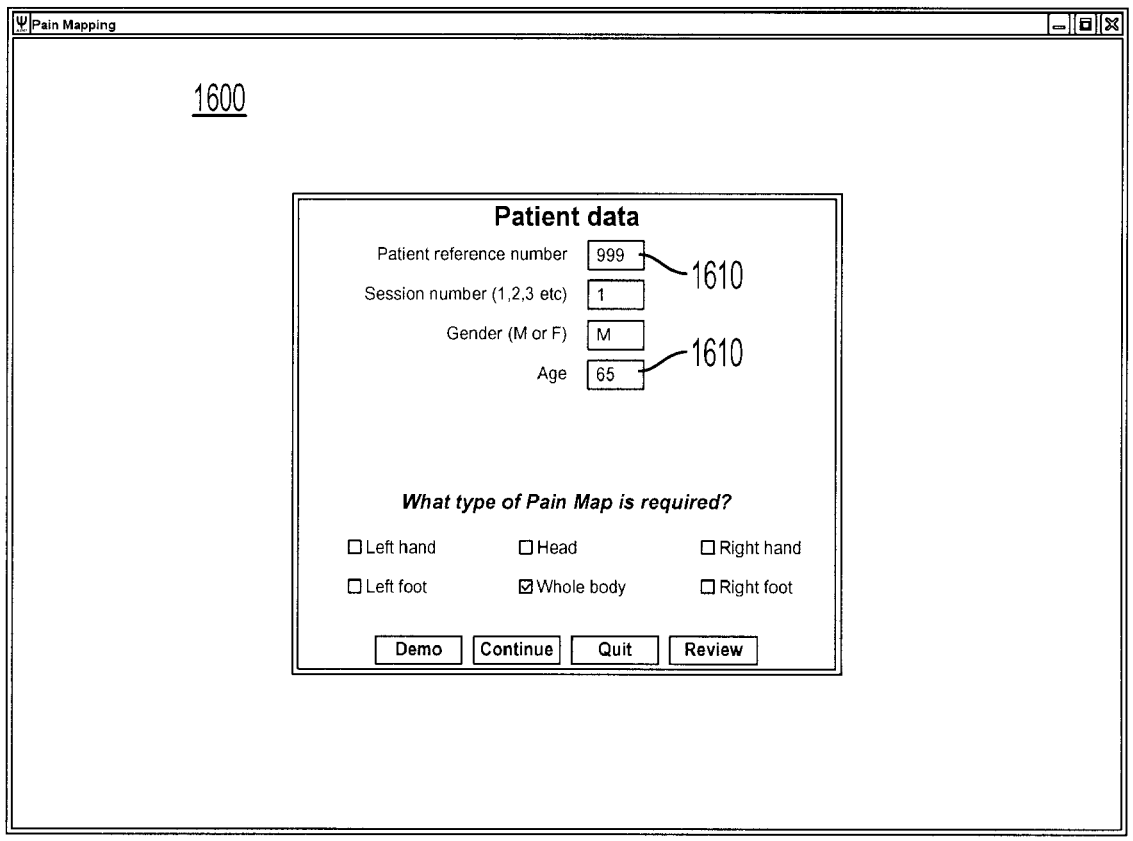
FIG. 16 is a screen shot generated by a symptom mapping system to collect patient data and indicate a type of pain map, consistent with one embodiment of the present invention.

Referring to FIG. 16, an embodiment of the symptom mapping system may also generate a data screen 1600, for example, before the user uses the system to generate a symptom map. The data screen 1600 may include fields 1610 for entering patient data, such as a patient reference number, session number, gender, age and/or other information. The data screen 1600 may also allow a user to select the type of symptom map to be generated, for example, based on a body portion. If the symptom mapping system is used to generate a pain map, for example, the user may select a type of pain map based on a portion of the body experiencing the pain (e.g., whole body, head, left hand, etc.).

Figure 17A:
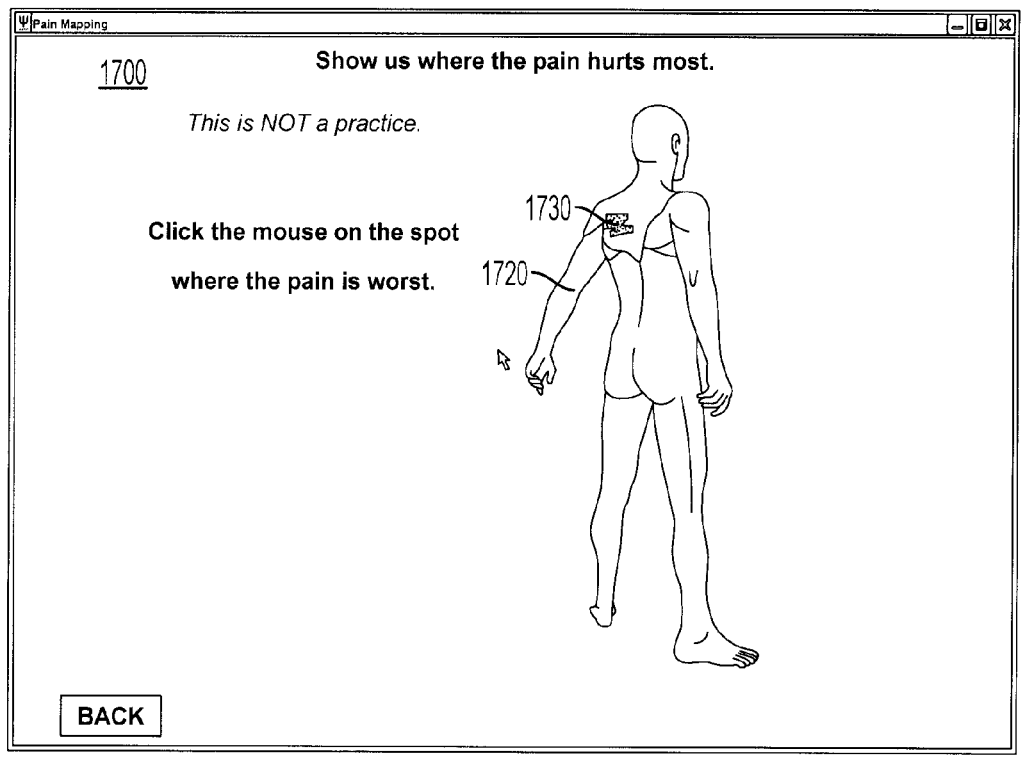
FIGS. 17A-17E are screen shots generated by a symptom mapping system using a three-dimensional body representation to map pain depth, consistent with yet another embodiment of the present invention.
Figure 17B:
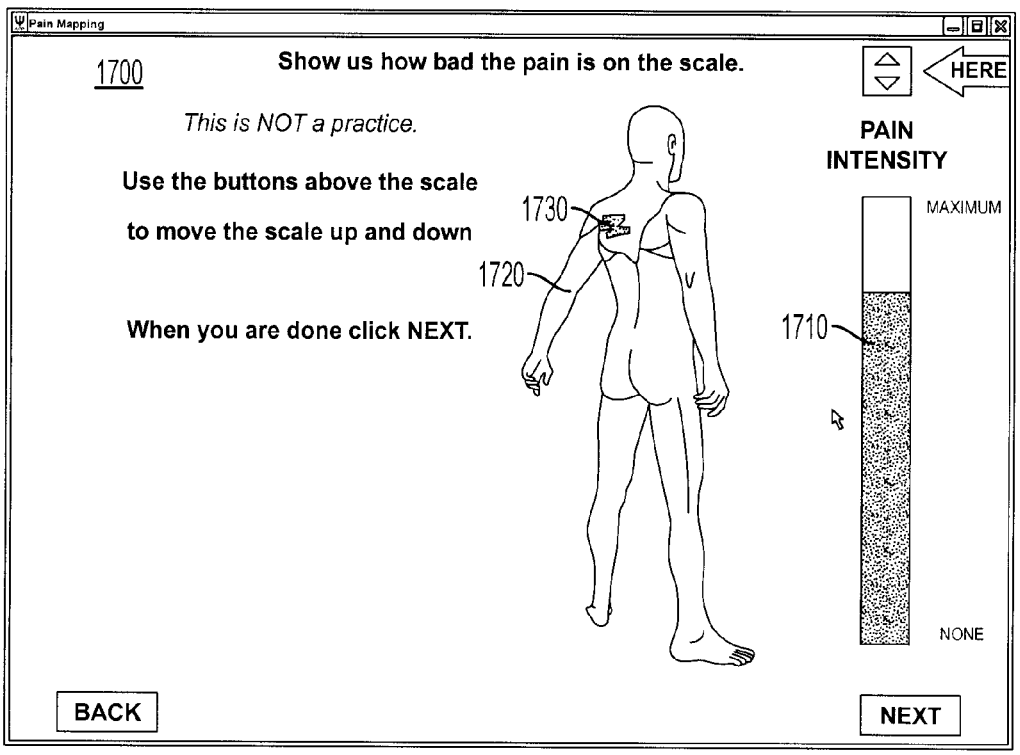
Figure 17C:
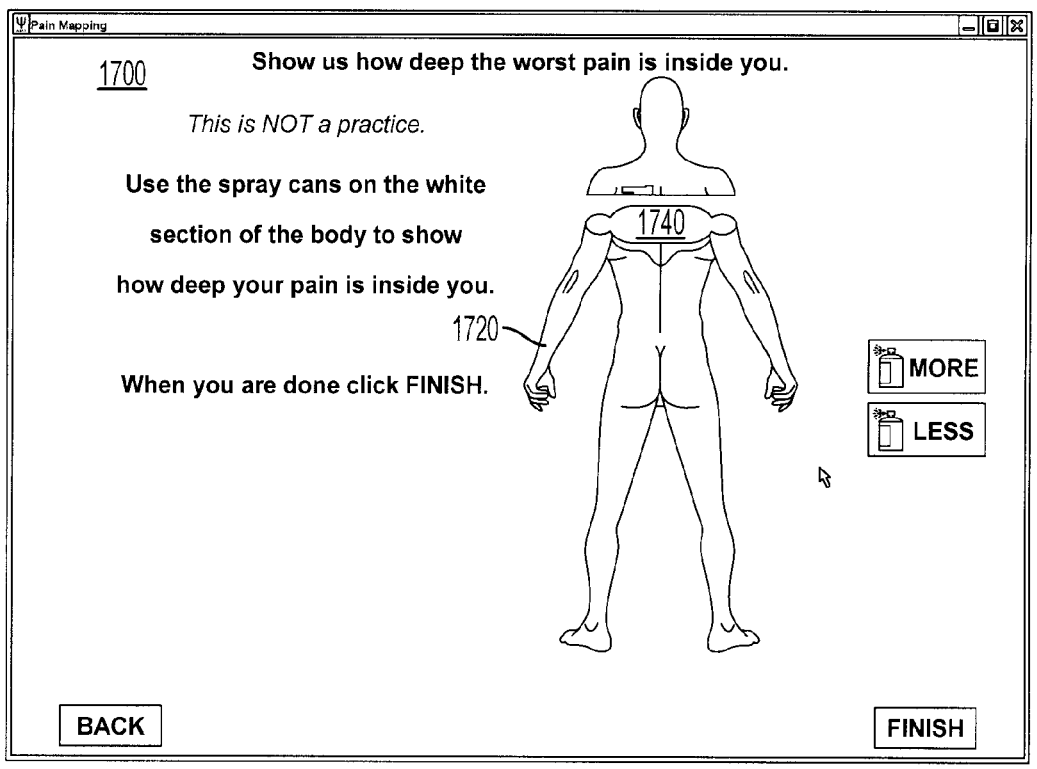
Figure 17D:
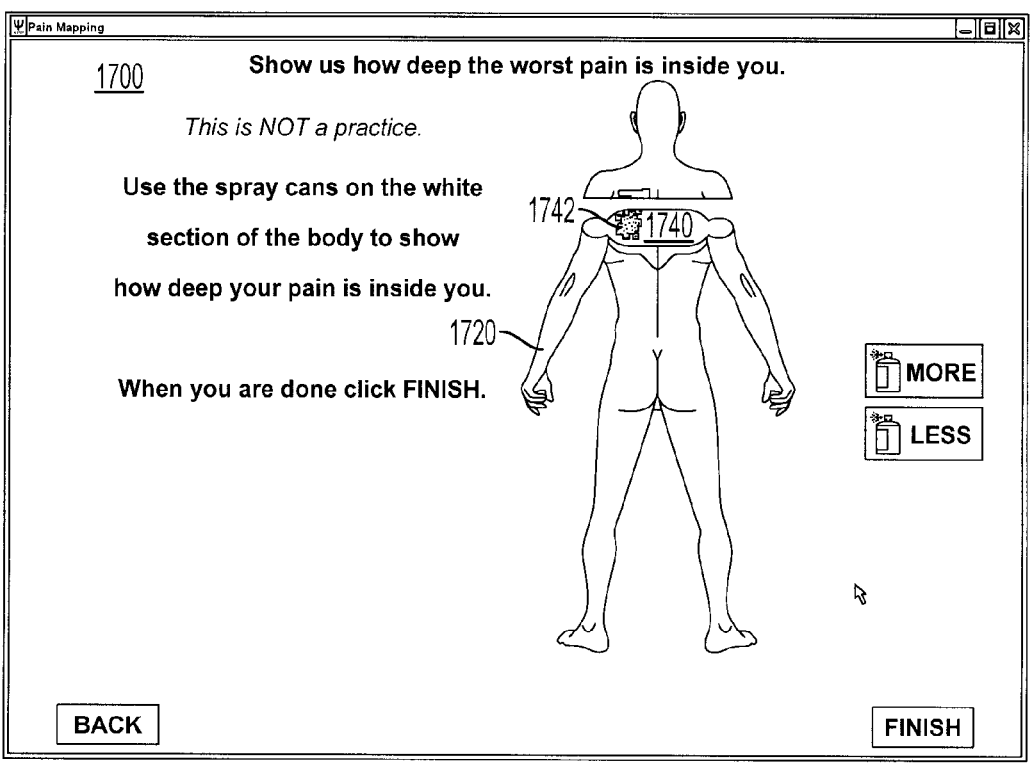

Referring to FIGS. 17A-17E, a further embodiment of a symptom mapping system for mapping pain depth is described in greater detail. In general, a user may select a pain location on a body representation (FIGS. 17A and 17B) and the symptom mapping system may display a cross-section of the body representation at the user-selected pain location (FIGS. 17C and 17D). The user may then select pain depth locations on the cross-section of the body representation to delineate a user-defined pain depth region on the cross-section (FIG. 17D).

According to one embodiment of pain depth mapping, a symptom mapping screen 1700 generated by the symptom mapping system may include a three-dimensional body representation 1720 depicting body surfaces in addition to an outline of the body. The three-dimensional body representation 1720 may be displayed and manipulated (e.g., rotated) to show different views, for example, as described above. According to other embodiments, a symptom mapping system for mapping pain depth may also be implemented with a two-dimensional representation of a body or portions of a body, as described above.

As shown in FIGS. 17A and 17B, the user may define one or more pain regions 1730 on the body representation 1720. If the body representation 1720 is a three-dimensional body representation, the pain region(s) 1730 appears to be on an outside surface of the body representation 1720. The pain region 1730 may be defined using symptom representations representing both the location and intensity of the pain experienced by the user, for example, as described above. After defining the pain region 1730, the user may select a maximum pain location within the pain region 1730. The user may further quantify the pain intensity at the maximum pain location, for example, using a visual analog scale 1710 or other technique such as those described above.

The maximum pain location selected by the user may also be the pain location at which the pain depth is defined. In other embodiments, the user may select a pain location for mapping pain depth without first defining a pain region on the outside surface of the body representation. When a pain location (e.g., a maximum pain location within a defined pain region) is selected, the symptom mapping system may display a cross section 1740 of the body representation 1720 at the selected location, as shown in FIG. 17C. In the exemplary embodiment, the body representation 1720 is separated at that location and a perspective view of the cross-section 1740 is shown. The cross-section 1740 thus appears as a surface that extends through the body representation 1720. The cross-section 1740 may also be shown without separating the body representation 1720, for example, using an outline of the cross-section and a different color to show the surface of the cross-section. Although the exemplary embodiment, shows a horizontal cross-section, the cross-section may be displayed vertically or along any direction relative to the body representation. The cross-section may be displayed essentially at any location on the body representation and along any axis relative to the body portion.

The user may then define one or more pain depth regions 1742 on the cross-section 1740 of the body representation, as shown in FIG. 17D. The pain depth regions 1742 may be defined according to any of the techniques described above for defining symptom regions on a body representation. For example, the pain depth region 1742 may include symptom representations displayed on the cross-section 1740 representing both pain location and intensity. The pain intensity within the pain depth region 1742 may be represented by color and/or density. The user may define multiple pain regions and/or pain depth regions at multiple locations on the body representation 1720.

Figure 17E:
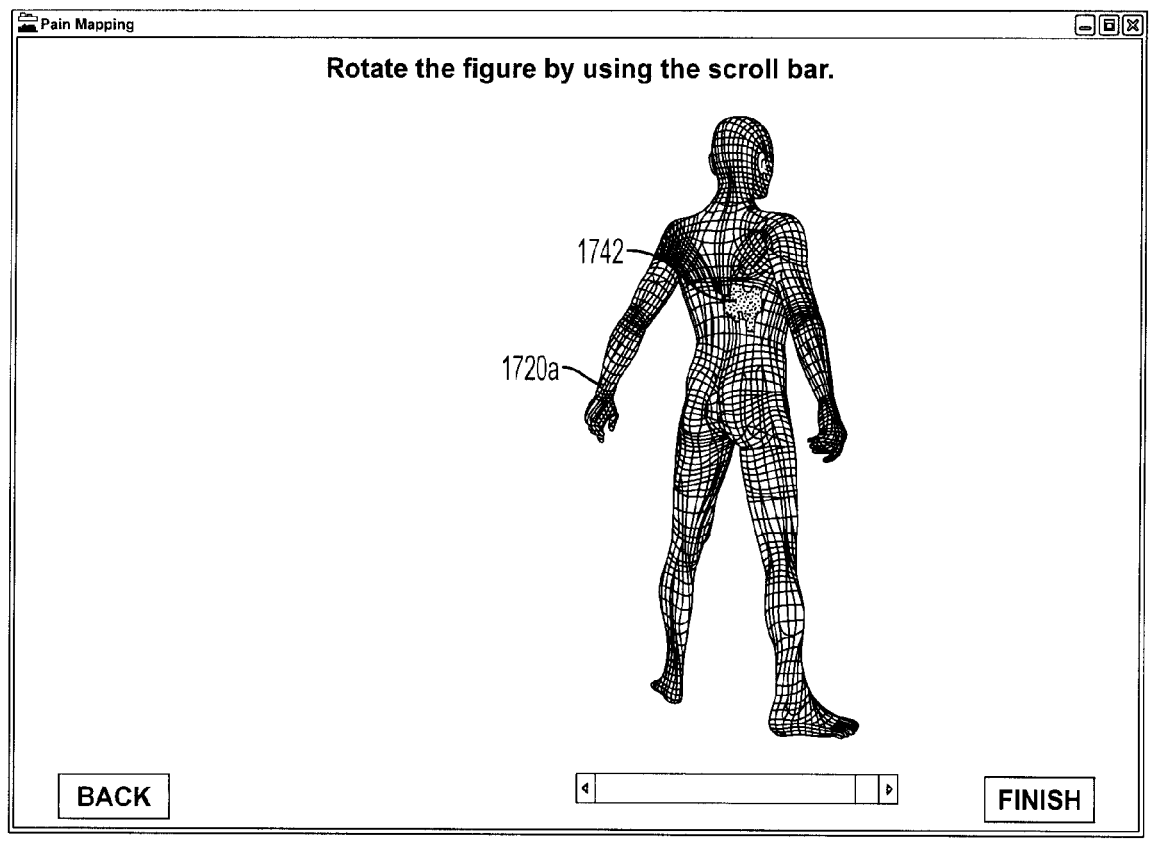

The one or more pain regions 1730 and the one or more pain depth regions 1742 defined by the user together form a pain map. The pain map may be reviewed by a user, such as the user associated with the pain map (i.e., the patient) or by another user (e.g., physician or medical worker). A pain region 1730 may be shown on an outside surface of the body representation 1720 and a pain depth region 1742 may be shown inside the body representation 1720. The outside pain region 1730 and the inside pain depth region 1742 may also be shown as the user causes the body representation 1720 to rotate, for example, as described above. As shown in FIG. 17E, for example, a three dimensional body representation 1720a may be shown as a "wire frame" model so that the pain depth region 1742 is perceived as being inside the body representation 1720a. The three dimensional body representation 1720a may be rotated, as described above, to allow the pain depth region 1742 to be viewed from different perspectives of the body, which assists the reviewer in evaluating the pain map.

Figure 18:
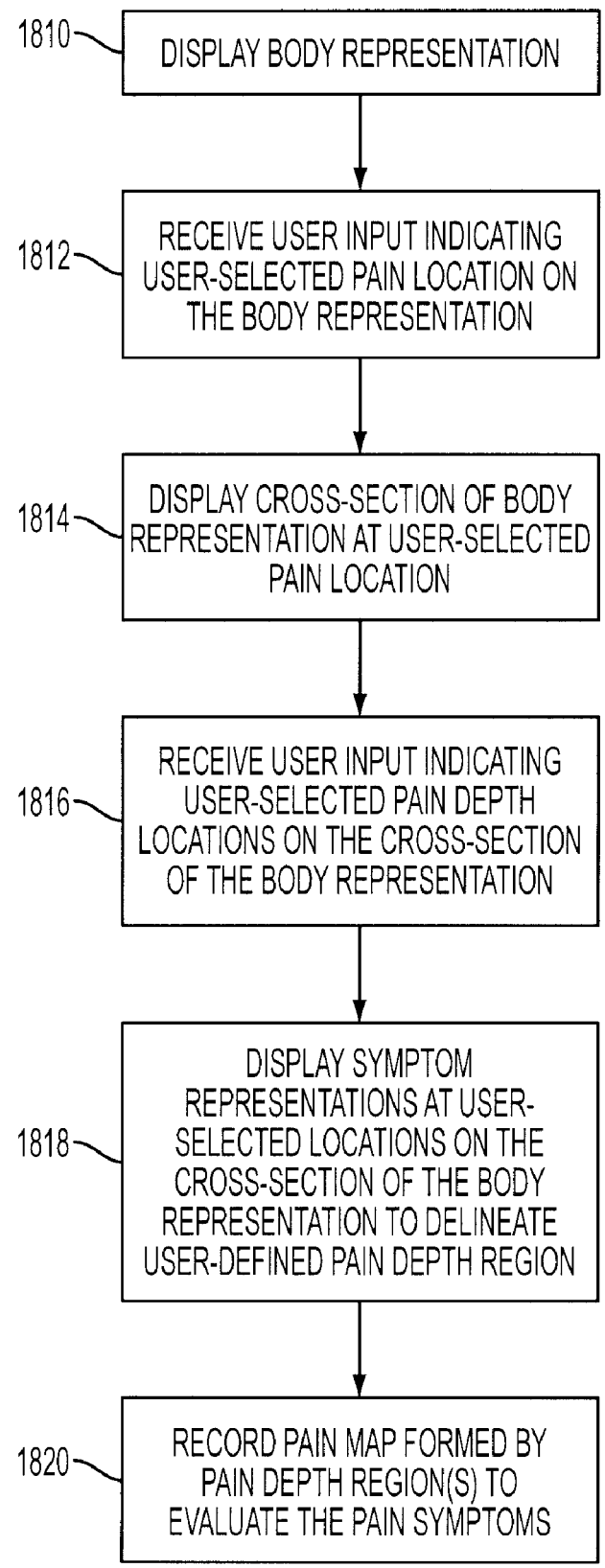
FIG. 18 is a flow chart illustrating one embodiment of a pain depth mapping method.

FIG. 18 illustrates one embodiment of a pain depth mapping method. This embodiment of the pain depth mapping method includes displaying 1810 one or more body representations. The body representation(s) may be displayed as two-dimensional or three-dimensional body representation(s) representing at least a portion of a user's body, as described above. The method may also include receiving 1812 a pain location user input indicating a user-selected pain location on the body representation, such as a maximum pain location within a user-defined pain region. The user-selected pain location may correspond to the location of an indicator, such as a cursor, controlled by a user input device while the user input device is activated. The method may further include displaying 1814 a cross-section of the body representation at the user-selected pain location.

After displaying the cross-section, the method may then receive 1816 a pain depth user input indicating user-selected pain depth locations on the cross-section of the body representation. The user-selected pain depth locations may correspond to the location of an indicator, such as a cursor, controlled by a user input device while the user input device is activated. The method may further include displaying 1818 symptom representations at the user-selected pain depth locations on the cross-section of the body representation to delineate at least one user-defined pain depth region. The symptom representations may include solid figures having a color indicating intensity of the symptom or may include a pattern of dots with color density indicating intensity of the symptom, as described above.

The method may further include recording 1820 a pain map formed by the pain depth region(s) to evaluate the pain experienced by the user. Recording a symptom map may include recording image files and/or data used to recreate the pain map including the body representation and the pain depth region(s) defined on the body representation. The data recorded for a pain depth region may include coordinates of symptom representations in the x, y and z axes. Other data associated with the pain map (e.g., patient data) may also be recorded.

Accordingly, embodiments of the present invention may be used to map pain depth. Consistent with one embodiment, a computerized method of mapping pain depth includes displaying at least one body representation on a display. The body representation represents at least a portion of the body of the user. This embodiment of the method further includes receiving at least one pain location user input indicating at least one user-selected pain location on the body representation. The pain location user input is generated by activating a user input device while an indicator is located at the user-selected location on the body representation corresponding to a location of pain experienced by the user. This embodiment of the method further includes displaying a cross-section of the body representation at the user-selected location and receiving at least one pain depth user input indicating user-selected pain depth locations on the cross-section of the body representation. The pain depth user input is generated by continuously activating a user input device for a period of time while moving an indicator across the user-selected pain depth locations on the cross-section of the body representation corresponding to pain depth experienced by the user within the body. This embodiment of the method further includes displaying symptom representations at the user-selected pain depth locations on the cross-section of the body representation in response to the pain depth user input. The symptom representations are displayed as the indicator moves across the user-selected pain depth locations to delineate a user-defined pain depth region at least partially filled in with the symptom representations on the cross-section of the body representation. This embodiment of the method further includes recording a pain map formed by at least one user-defined pain depth region to evaluate the pain experienced by the user.

Consistent with a another embodiment, a computerized method of mapping pain depth includes displaying at least one three-dimensional body representation on a display, wherein the body representation represents at least a portion of the body of the user. This embodiment of the method further also receiving a body positioning user input indicating a direction of movement of the three-dimensional body representation and displaying at least one different perspective of the three-dimensional representation in response to the body positioning user input and corresponding to the associated direction of movement. This embodiment of the method further includes receiving at least one pain region user input indicating user-selected locations on the body representation. The pain region user input is generated by continuously activating a user input device for a period of time while moving an indicator across the user-selected locations on the body representation corresponding to locations of pain experienced by the user. This embodiment of the method further includes displaying symptom representations at the user-selected locations on the body representation in response to the pain region user input. The symptom representations are displayed as the indicator moves across the user-selected locations to delineate a user-defined pain region at least partially filled in with the symptom representations on the body representation, and the symptom representations represent locations of the pain within the pain region.

This embodiment of the method further includes receiving at least one maximum pain location user input indicating at least one user-selected maximum pain location within the pain region on the body representation. The user input is generated by activating a user input device while an indicator is located at the user-selected maximum pain location on the body representation corresponding to a location of maximum pain experienced by the user. This embodiment of the method further includes displaying a cross-section of the body representation at the user-selected maximum pain location and receiving at least one pain depth user input indicating user-selected pain depth locations on the cross-section of the body representation. The user input is generated by continuously activating a user input device for a period of time while moving an indicator across the user-selected locations on the cross-section of the body representation corresponding to locations of pain experienced by the user within the body. This embodiment of the method further includes displaying symptom representations at the user-selected pain depth locations on the cross-section of the body representation in response to the user input. The symptom representations are displayed as the indicator moves across the user-selected pain depth locations to delineate a user-defined pain depth region at least partially filled in with the symptom representations on the body representation. At least one user-defined pain region and at least one pain depth region form a symptom map used to evaluate the pain experienced by the user.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. A computerized method of mapping pain depth, the method comprising:
   displaying at least one body representation on a display, wherein the body representation represents at least a portion of the body of the user;

receiving at least one pain location user input indicating at least one user-selected pain location on the body representation, the pain location user input being generated by activating a user input device while an indicator is located at the user-selected location on the body representation corresponding to a location of pain experienced by the user;

displaying a cross-section of the body representation at the user-selected location;

receiving at least one pain depth user input indicating user-selected pain depth locations on the cross-section of the body representation, the pain depth user input being generated by continuously activating a user input device for a period of time while moving an indicator across the user-selected pain depth locations on the cross-section of the body representation corresponding to pain depth experienced by the user within the body;

displaying symptom representations at the user-selected pain depth locations on the cross-section of the body representation in response to the pain depth user input, wherein the symptom representations are displayed as the indicator moves across the user-selected pain depth locations to delineate a user-defined pain depth region at least partially filled in with the symptom representations on the cross-section of the body representation; and recording a pain map formed by at least one user-defined pain depth region to evaluate the pain experienced by the user.

2. The method of claim 1 wherein displaying the symptom representations includes displaying symptom representations with different color densities to represent different intensities of pain.

3. The method of claim 2 wherein each of the symptom representations includes a predetermined pattern of dots, and wherein the color densities of the symptom representations are based, at least in part, on the number of the dots displayed in a region.

4. The method of claim 2 wherein each of the symptom representations includes at least one dot having a variable shade, and wherein the color densities of the symptom representations are based, at least in part, on the shade of the dots displayed in a region.

5. The method of claim 1 further including comparing the symptom map to a library of data to determine a diagnosis, wherein the library of data includes data previously recorded for other patients.

6. The method of claim 1 wherein receiving at least one pain depth user input includes receiving at least one user input generated by holding down a button on a mouse while moving a cursor controlled by the mouse over the locations on the display, and wherein the symptom representations are displayed at the locations of the cursor on the display as the cursor moves over the locations.

7. The method of claim 1 further comprising:
receiving at least one erasure user input indicating at least one user-selected location with at least one symptom representation to be erased; and
erasing the at least one symptom representation in response to the erasure user input such that the user-defined pain depth region is modified.

8. The method of claim 1 wherein displaying the body representation includes displaying a three-dimensional body representation representing at least a portion of the body.

9. The method of claim 1 further comprising:
receiving a body positioning user input indicating a direction of movement of the three-dimensional body representation; and displaying at least one different perspective of the three-dimensional body representation in response to the body positioning user input and corresponding to the direction of movement.

10. The method of claim 1 further comprising, prior to receiving at least one pain location user input:
receiving at least one pain region user input indicating user-selected locations on the body representation, the pain region user input being generated by continuously activating a user input device for a period of time while moving an indicator across the user-selected locations on the body representation corresponding to locations of pain experienced by the user; and
displaying symptom representations at the user-selected locations on the body representation in response to the pain region user input, wherein the symptom representations are displayed as the indicator moves across the user-selected locations to delineate a user-defined pain region at least partially filled in with the symptom representations on the body representation, wherein the symptom representations represent locations of the pain within the pain region.

11. The method of claim 10 wherein receiving the at least one pain location user input includes receiving a maximum pain location user input indicating a user-selected location of maximum pain within the pain region.

12. The method of claim 10 wherein the symptom representations represent different intensities of the pain within the pain region.

13. A non-transitory machine-readable medium whose contents cause a computer system to perform a method of mapping pain depth according to claim 1.

14. A computerized method of mapping pain depth, the method comprising:
displaying at least one three-dimensional body representation on a display, wherein the body representation represents at least a portion of the body of the user;
receiving a body positioning user input indicating a direction of movement of the three-dimensional body representation;
displaying at least one different perspective of the three-dimensional representation in response to the body positioning user input and corresponding to the associated direction of movement;
receiving at least one pain region user input indicating user-selected locations on the body representation, the pain region user input being generated by continuously activating a user input device for a period of time while moving an indicator across the user-selected locations on the body representation corresponding to locations of pain experienced by the user;
displaying symptom representations at the user-selected locations on the body representation in response to the pain region user input, wherein the symptom representations are displayed as the indicator moves across the user-selected locations to delineate a user-defined pain region at least partially filled in with the symptom representations on the body representation, wherein the symptom representations represent locations of the pain within the pain region;
receiving at least one maximum pain location user input indicating at least one user-selected maximum pain location within the pain region on the body representation, the user input being generated by activating a user input device while an indicator is located at the user-selected maximum pain location on the body representation corresponding to a location of maximum pain experienced by the user;

displaying a cross-section of the body representation at the user-selected maximum pain location;

receiving at least one pain depth user input indicating user-selected pain depth locations on the cross-section of the body representation, the user input being generated by continuously activating a user input device for a period of time while moving an indicator across the user-selected locations on the cross-section of the body representation corresponding to locations of pain experienced by the user within the body; and displaying symptom representations at the user-selected pain depth locations on the cross-section of the body representation in response to the user input, wherein the symptom representations are displayed as the indicator moves across the user-selected pain depth locations to delineate a user-defined pain depth region at least partially filled in with the symptom representations on the body representation, and wherein at least one user-defined pain region and at least one pain depth region form a symptom map used to evaluate the pain experienced by the user.

15. The method of claim 14 wherein the intensities of the symptoms are represented by user-defined color densities of the symptom representations.

16. The method of claim 15 wherein each of the symptom representations includes a predetermined pattern of dots, and wherein the color density of the symptom representations is based, at least in part, on a number of the dots displayed within a region.

17. The method of claim 15 wherein each of the symptom representations includes at least one dot having a variable shade, and wherein the color density of the symptom representations is based, at least in part, on the shade of the dots displayed with a region.

18. The method of claim 15 comprising:

receiving at least one user input indicating less intensity at user-selected locations on the body representation, the user input being generated by activating the user input device while moving the indicator across user-selected locations on the body representation corresponding to locations where symptom intensity is to be decreased; and decreasing the color density of the symptom representations at the user-selected locations in response to the user input.

19. The method of claim 14 wherein the symptom representations are not displayed at locations outside of the body representation even when the indicator moves outside of the body representation.

20. The method of claim 14 further comprising quantifying symptom intensity for at least one location on at least one user-defined symptom region forming the symptom map.

21. A non-transitory machine-readable medium whose contents cause a computer system to perform a method of mapping pain depth according to claim 14.

* * * * *